(12) United States Patent
Hastings et al.

(10) Patent No.: US 7,410,497 B2
(45) Date of Patent: Aug. 12, 2008

(54) STIMULATION OF CELL GROWTH AT IMPLANT SURFACES

(75) Inventors: Roger N. Hastings, Maple Grove, MN (US); William J. Drasler, Minnetonka, MN (US); Mark Lynn Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 418 days.

(21) Appl. No.: 11/011,263

(22) Filed: Dec. 14, 2004

(65) Prior Publication Data

US 2006/0129216 A1    Jun. 15, 2006

(51) Int. Cl.
*A61F 2/06* (2006.01)
*A61N 1/02* (2006.01)

(52) U.S. Cl. .................................. 623/1.11; 607/115

(58) Field of Classification Search ........ 623/1.11–1.42, 623/23.76, 11.11; 606/505; 607/115
See application file for complete search history.

(56) References Cited

U.S. PATENT DOCUMENTS

| | | | |
|---|---|---|---|
| 4,751,928 A | 6/1988 | Hallon et al. | 128/644 |
| 4,919,138 A | 4/1990 | Nordenstroöm et al. | 128/421 |
| 5,344,440 A | 9/1994 | Stephen | 607/139 |
| 5,433,735 A | 7/1995 | Zanakis et al. | 607/50 |
| 5,674,267 A | 10/1997 | Mir et al. | 607/72 |
| 6,009,347 A | 12/1999 | Hofmann | 604/21 |
| 6,099,832 A | 8/2000 | Mickle et al. | 424/93.21 |
| 6,120,493 A | 9/2000 | Hofmann | 604/506 |
| 6,317,631 B1 | 11/2001 | Ben-Haim et al. | 607/9 |
| 6,463,323 B1 | 10/2002 | Conrad-Vlasak et al. | 607/2 |
| 6,810,286 B2 | 10/2004 | Donovan et al. | 607/2 |
| 6,937,736 B2 * | 8/2005 | Toda | 381/190 |
| 2002/0138100 A1 | 9/2002 | Stoll et al. | 607/1 |
| 2002/0169480 A1 | 11/2002 | Zhu et al. | |
| 2002/0177224 A1 | 11/2002 | Madry et al. | 435/325 |
| 2003/0233124 A1 | 12/2003 | Hara et al. | 607/3 |
| 2003/0233131 A1 | 12/2003 | Kramer et al. | 607/9 |
| 2004/0222102 A1 | 11/2004 | George et al. | 205/118 |
| 2004/0236170 A1 | 11/2004 | Kim | 600/16 |

(Continued)

FOREIGN PATENT DOCUMENTS

WO    WO 00/78375 A1    12/2000

(Continued)

OTHER PUBLICATIONS

J.J. Ross et al., "ECM gene expression correlates with in vitro tissue growth and development in fibrin gel remodeled by neonatal smooth muscle cells," *Matrix Biology*, 22 (2003), pp. 477-490.

(Continued)

*Primary Examiner*—Suzette J Gherbi
(74) *Attorney, Agent, or Firm*—Mayer & Williams PC; David B. Bonham, Esq.; Keum J. Park, Esq.

(57) ABSTRACT

The present invention is directed to medical devices that contain at least one tissue contacting surface that is configured to undergo a variation in surface charge in response to a time-dependent signal. Such a variation in surface charge is provided, for example, to enhance or inhibit cellular growth adjacent to, on, or within the at least one tissue contacting surface.

69 Claims, 25 Drawing Sheets

Spiral Film Pattern

U.S. PATENT DOCUMENTS

2005/0060021 A1* 3/2005 O'Brien et al. ............ 623/1.15
2006/0089709 A1* 4/2006 Helmus ..................... 623/1.44
2006/0129050 A1* 6/2006 Martinson et al. .......... 600/505

FOREIGN PATENT DOCUMENTS

WO  WO 2004/080887 A1  9/2004

OTHER PUBLICATIONS

Naren Dubey, Paul C. Letourneau, and Robert T. Tranquillo, "Investigation of the Mechanism of Contact Guidance of Neurite Growth Cones In Magnetically-Aligned Collagen Gels", Proceedings of the First Joint BMES/EMBS Conference, *Serving Humanity, Advancing Technology*, Atlanta, GA, USA, Oct. 13-16, 1999, p. 39.

Michael R. Neidert, Jeremiah J. Wille, Robert T. Tranquillo, "Development and Characterization of Improved Tissue Engineered Valve-Equivalents using Chemical and Mechanical Signaling", Proceedings of the Second Joint BMES/EMBS Conference, Houston, TX, USA, Oct. 23-26, 2002, pp. 858-859.

Elizabeth A. Thomas, "Engineers Aim to Mend Broken Hearts", Massachusetts Institute of Technology, http://web.mit.edu/newsoffice/2004/heart.html, downloaded May 25, 2005.

Robert T. Tranquillo, "Cardiovascular and Neural Tissue Engineering", University of Minnesota, Department of Biomedical Engineering, http://www1.umn.edu/bme/people/tranquillo2.html, downloaded May 25, 2005.

Sarah Graham, "Electric Signals Key to Culturing Heart Tissue", ScientificAmerica.com.news. Dec. 14, 2004. http://www.sciam.com/article.cfm?articleID=00426DE-095B-11BE-895B83414B7F0000 Downloaded May 25, 2005.

Article prepared by Biotech Week editors from staff and other reports. "Engineers are Significantly Closer to Mending Broken Heartts", NewsRxBiotech *via NewsEdge Corporation*, Dec. 29, 2004. Copyright © 2004NewsRXBiotech, downloaded Mar. 18, 2005.

\* cited by examiner

Spiral Film Pattern

Circular Film Pattern

Segmented Film Option (magnified view)

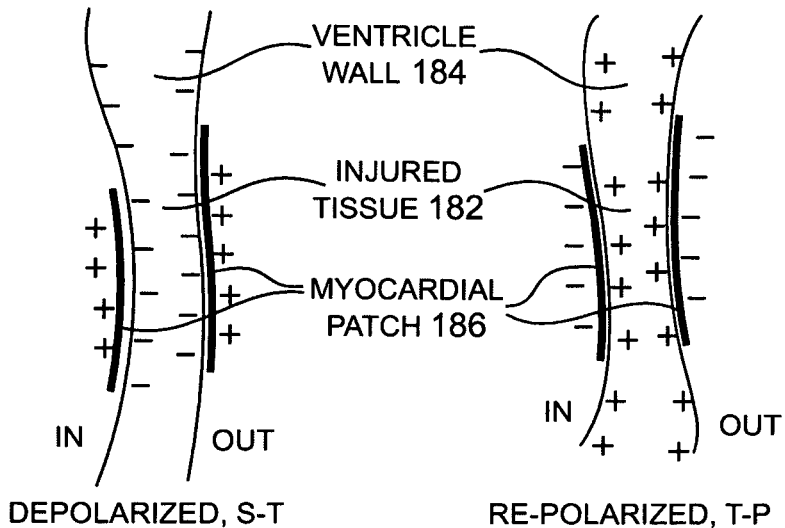
DEPOLARIZED, S-T
FIG. 18a
RE-POLARIZED, T-P
FIG. 18b
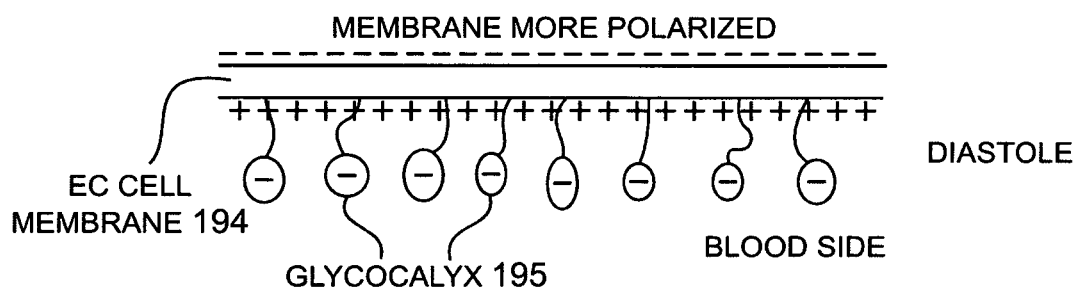
FIG. 19a
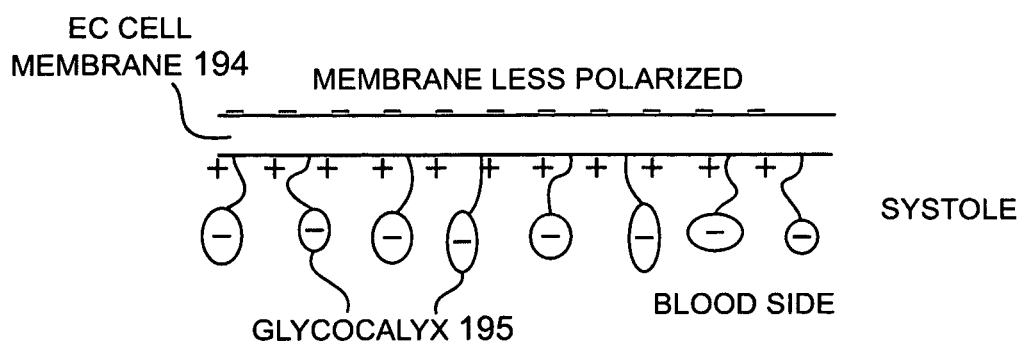
FIG. 19b

STIMULATION OF CELL GROWTH AT IMPLANT SURFACES

FIELD OF THE INVENTION

The present invention relates generally to implants for living organisms, including humans.

BACKGROUND

A large body of literature describes the function and fate of blood-contacting surfaces of implanted structures, including Left Ventricular Assist Devices (LVADs), Totally Artificial Hearts (TAHs), synthetic arterial grafts, heart valves, stents, indwelling catheters and filters, and plugs for septal defects and occlusion of aneurysms and appendages. Early design goals for these surfaces were to create a biocompatible structure upon which blood would not become activated or result in inflammatory, thrombotic, or immune responses. While the issue of biocompatibility has found numerous material solutions, the creation of blood-contacting surfaces that remain clean and free of tissue over time has not occurred. Early attempts to create smooth, non-activating surfaces failed, even though surface imperfections were reduced in size below ten microns, and very hydrophobic materials, such as Teflon, were employed.

The body's response to an implanted foreign object is to first coat the object with a layer of protein, then to recruit macrophages and fibroblasts that engulf the object, or cover the object in a layer of collagen. The collagen "bag" around the object is nearly acellular (with some fibroblasts), and is generally not well vascularized.

Protein coatings form on implanted prostheses in contact with blood, followed by platelet adhesion and fibrosis. This growth is often referred to as a "pseudo-intima." Smooth muscle cells (SMCs) and endothelial cells (ECs) may grow over the base coating creating a "neo-intima." Some researchers continue to pursue surfaces with smoothness at or below the one-micron level, with the goal of reduced or minimal protein adhesion, and subsequently resulting in an overall thinner layer of pseudo-intima. This approach has been more effective in high flow and high shear rate settings.

The pseudo-intima, without an endothelial coating, is a potentially thrombogenic surface, subject to platelet adhesion, continued fibrotic deposition, and possibly calcification. Platelet adhesion is inhibited or eliminated by a healthy layer of ECs in contact with blood. The creation or formation of a blood contacting endothelial layer, with or without an underlying layer of SMCs, is the "holy grail" of surface implant science. The ECs actively inhibit platelet adhesion, and selectively pass nutrients and cells to and from the underlying tissues.

To date, no synthetic, blood-contacting surface material has been found that heals without incident in humans. For example, LVAD surfaces have been developed that form pseudo-intima, but with no evidence of an endothelial layer. These surfaces continue to grow and shed over time, maintaining an approximately constant thickness, but also remaining thrombogenic. While perhaps dozens of small-bore vascular graft materials have been proposed and tested, the failure rate for these devices has been poor in humans, with no clear evidence of healing of the blood-contacting surface. While EC seeded grafts and TE (tissue engineering) grafts may someday succeed in demonstrating long-term patency in humans, they may never become commercially viable. Various synthetic valves have been proposed, but none has been successfully demonstrated in humans. A need therefore exists for a synthetic material that spontaneously grows a continuous EC layer in a reasonably short period of time (weeks).

Because synthetic, blood contacting, human implant surfaces have failed to heal in applications such as small diameter arterial grafts, synthetic heart valves and blood pumps, alternative approaches have been taken, including vein grafts from the patient's legs for bypass, porcine or bovine tissue for heart valves, and rigid inert surfaces for valves and blood pumps. Vein grafts and animal tissue prostheses, however, can fail over time due to calcification, thrombosis and continuing atherosclerosis. Moreover, rigid inert surfaces require the patient to take anticoagulation medication indefinitely.

SUMMARY OF THE INVENTION

The present invention addresses these and other problems by providing medical devices that contain at least one blood contacting surface that is adapted to undergo a variation in surface charge in response to a time-dependent signal at a site of contact with a host. Medical devices that may benefit from variations in surface charge include, but are not limited to, vascular grafts, heart and venous valves, ventricular assist devices, stents, indwelling catheters and filters, pacemaker leads, and plugs for septal defects, aneurysms and heart appendages. Surface charges of native blood-contacting tissues, such as a degenerated aortic wall, may be established to encourage healing of the same.

Other aspects of the present invention will be apparent upon review of the following drawings in light of the detailed description.

BRIEF DESCRIPTION OF THE DRAWINGS

FIGS. 18a and 18b are schematic drawings of a stimulated myocardial patch covering an infarct zone during systole and diastole, respectively, according to an exemplary embodiment of the present invention.

FIGS. 19a and 19b are schematic drawings of membrane charge during diastole and systole, respectively, and including the fixed negative charge of the surface glycocalyx, according to an exemplary embodiment of the present invention.

DETAILED DESCRIPTION

Figure 1:
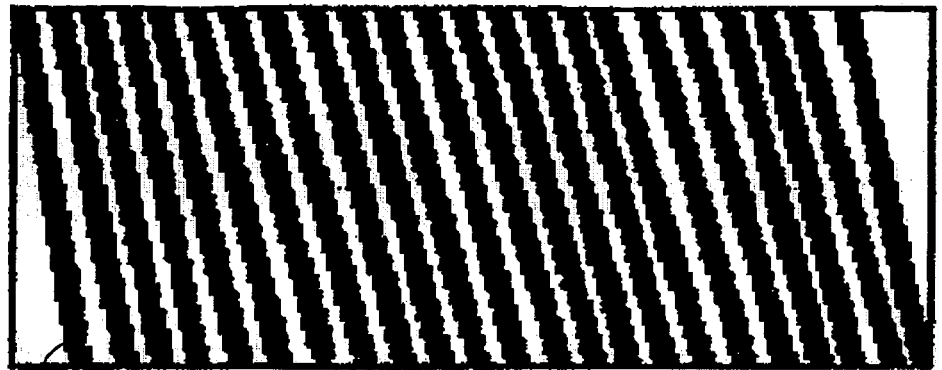
FIG. 1 depicts a circular pattern applied to a piezoelectric film in a vascular graft, according to an exemplary embodiment of the present invention.

The present invention is directed to medical devices that contain at least one tissue contacting surface that is configured to undergo a variation in surface charge in response to a time-dependent signal that is effective to enhance or inhibit cellular growth adjacent to, on, or within the at least one tissue contacting surface.

For example, variations in surface charge can be established using a number of techniques including phasic, electrical stimulation using one or more of the following techniques: (a) electrical techniques, for example, techniques in which an electrical potential is applied across two or more electrodes by directly (i.e., via conductors) or indirectly (e.g., via inductive or capacitive techniques) coupling the electrodes to a source of power, (b) electromechanical techniques, for example, by using materials such as piezoelectric or electrostrictive materials that produce a surface charge in response to mechanical deformation, or (c) by electromagnetic techniques, for example, by providing a magnetic field normal to the flow of ionic species within the body, which causes charge separation of the ionic species and thereby producing an electric field in vivo.

As will become apparent from the discussion to follow, as used herein, the phrase "electrical stimulation" includes active stimulation using a power source (e.g., by conductive, inductive and/or capacitive coupling), as well as by passive methods including electromechanical stimulation (e.g., using piezoelectric films), electromagnetic stimulation (e.g., based on the Hall effect), and so forth.

Surface charge can be established, for example, by creating a phasic potential difference (a) between a tissue contacting region of the device and an interior region of the device, (b) between two tissue contacting regions of the device, (c) between a tissue contacting region of the device and a location within the body of the patient (e.g., in the blood or other tissue, a location that is proximate to, i.e., within one cm of the device, or remote from the device), and (d) between a tissue contacting region of the device and a location external to the body of the patient.

By saying that a parameter is "phasic" it is meant that the parameter varies over time. In certain embodiments surface charge will vary over time in a substantially repetitive fashion, for example, in the form of a square wave, sinusoid, or other more complex waveforms. For example, variations in surface charge can be synchronized in some embodiments with an endogenous phasic signal, such as blood pressure, blood flow, an electrocardial signal, or any other signal that varies periodically with the heartbeat.

Cells targeted for promotion and/or inhibition of growth include, for example, (a) epithelial cells, such as keratinized and non-keratinized squamous endothelial cells, cuboidal epithelial cells, columnar epithelial cells, pseudostratified columnar epithelial cells, transitional epithelial cells and glandular epithelial cells, including those lining the heart, blood vessels, upper GI tract (e.g., cheek and esophagus), lower GI tract (e.g., stomach, intestines and colon), respiratory tract (e.g., trachea, bronchi, alveoli), urinary tract (e.g., the renal pelvis, ureters, bladder and urethra), the female reproductive tract (e.g., the uterus and fallopian tubes), ducts of the male reproductive system, various major body cavities (e.g., peritoneal, pleural, pericardial), sinusoids, lymphatics, glandular ducts, and so forth, (b) muscle cells, e.g., SMCs (which lie beneath epithelial cells in many body lumens such as many of those found in the vasculature, the genitourinary system, respiratory tract and gastrointestinal tract) and cardiomyocytes, (c) connective tissue cells such as fibroblasts, and (c) immature cells, such as totipotent, pluripotent, multipotent, and progenitor stem cells, for example, endothelial progenitor cells and endothelial stem cells, myoblasts, etc.

In various embodiments of the invention, electrical stimulation is used to promote cell growth, for example, growth of vascular epithelium. In this connection, and without wishing to be limited to a particular theory of operation, it has been proposed that using negatively charged blood-contacting surfaces on implants will repel negatively charged proteins and platelets in the blood, leaving a clean surface. It has also been proposed that a static negative charge placed in a wound promotes migration of epithelial cells into the wound from the wound margin, and accelerates healing. Interestingly, the magnitude of the electric field required to promote healing is on the order of d.c. electric fields that are generated by the tissue itself, as measured at the wound margins.

Attempts to date at chemical surface modifications designed to expose negative charge groups when hydrated by blood have been unable to prevent pseudo-intima formation or to promote the growth of ECs on the implant surface. Failure may be due to a static surface charge density that is either too large or too small.

On the other hand, failure may be due to the fact that polarizable tissue, such as SMCs and ECs lining native cardiovascular surfaces, undergo phasic variations in surface membrane potential, and that phasic surface stimulation is therefore required to promote healing. Such variations in surface membrane potential may be synchronized with the myocardial depolarization wave directly. Or, phasic variations may be caused by the membrane potential response to other endogenous parameters such as blood pressure variations.

Therefore, one aspect of the present invention provides medical devices with a negatively charged surface during systole in combination with a neutral or positively charged surface during diastole to promote EC growth.

Electrical stimulation according to the invention is possible, for example, using an implanted stimulator (similar, for example, to those used in conjunction with pacemakers), or with an ex vivo stimulator (e.g., coupled via percutaneous electrical leads, induction, etc.). Highly complex electrical stimulation waveforms can be implemented using such devices.

However, electrical stimulation according to the invention is also possible, for example, using passive devices which are also disclosed herein for this purpose.

Stimulation Using Electromechanical Transducing Materials

In this regard, and according to an aspect of the present invention, a piezoelectric or electrostrictive material can be employed to encourage EC growth on the medical device. In some embodiments, the piezoelectric or electrostrictive material is placed on the tissue contacting (e.g., blood contacting) surfaces of the implant device. Thus, according to another aspect of the present invention, changes in the blood pressure are used to create a charge separation and voltage across a piezoelectric or electrostrictive material (i.e., an electric field is created). Since it is believed that ECs migrate toward the negative pole of an applied electric field, the creation of a phasic negative surface charge is expected to encourage ingrowth of endothelium from the margins of the implant and/or deposition of ECs or epithelial progenitor cells from the blood. In addition, the phasic charge on the implant surface is designed to mimic phasic variations in the native SMC substrate membrane potential, creating a more natural substrate to support continued healthy functioning of the new EC layer.

Piezoelectric and electrostrictive materials are materials that mechanically deform upon application of an external electric field and, conversely, that generate an electric charge when they are mechanically deformed. As a general rule, electrostrictive materials exhibit strains proportional to the square of the applied electric field strength (and vice versa), whereas piezoelectric materials exhibit strains that are directly proportional to the applied field strength. The important characteristic for the materials used herein is that they generate an electric charge in response to deformation (strain), also referred to herein as "electromechanical transducing materials". Such electromechanical transducing materials may be structures formed of a single material or of composite materials, such as blends of different materials, layers of different materials (e.g., metal-insulator-metal structures), and innumerable other combinations. A few specific examples of materials that generate an electric charge in response to deformation include: polymer materials such as polyvinylidene fluoride (PVDF) and its copolymers with trifluoroethylene and tetrafluoroethylene, nylons with an odd number of carbons (e.g., PA 7), polyvinylchloride (PVC), polyphenylethernitrile (PPEN) and polyacrylonitrile (PAN), among others; ceramic materials such as Lead Zirkonate Titanate PZT-5, Lead Titanate PT, Lead Metaniobate $PbNb_2O_6$, barium titanate and quartz, among others; metallic piezoelectric materials; as well as combinations thereof.

A properly designed polyvinylidene fluoride (PVDF) copolymer film is a particularly beneficial example of a piezoelectric film which is capable of generating a surface charge variation with blood pressure (diastolic to systolic) in accordance with the present invention, because the surface charge variation with blood pressure is comparable to surface charge variations on native cell membranes.

Figure 2:
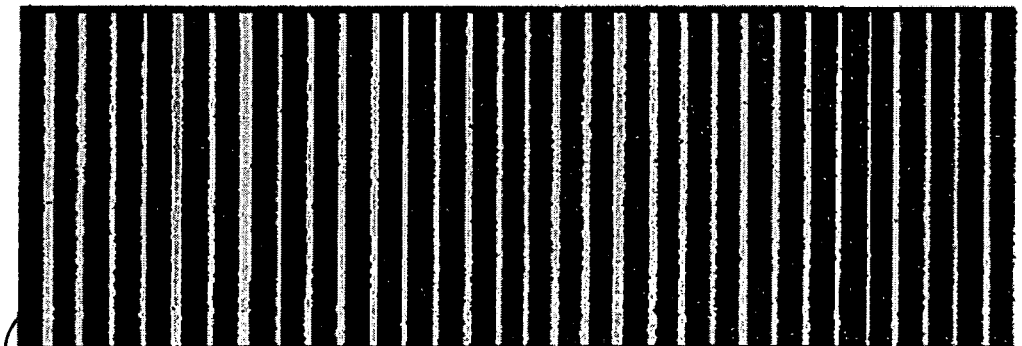
FIG. 2 depicts a spiral pattern applied to a piezoelectric film in a vascular graft, according to an exemplary embodiment of the present invention.
Figure 3:
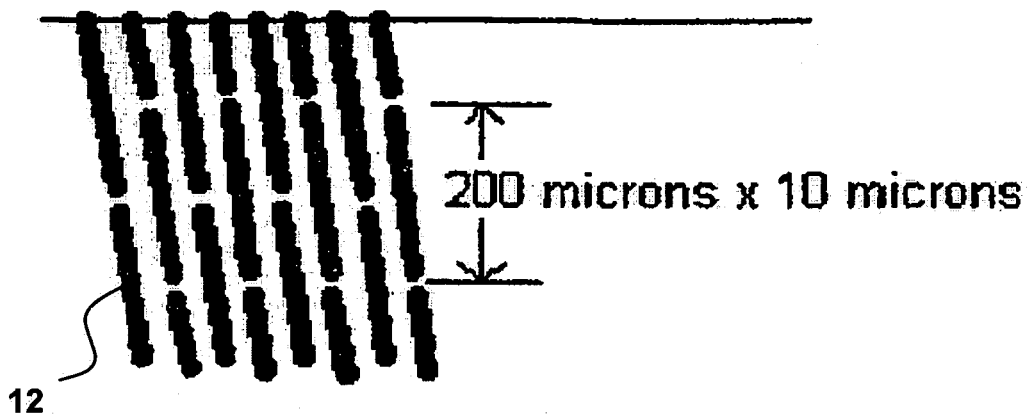
FIG. 3 depicts a segmented spiral pattern applied to a piezoelectric film in a vascular graft, according to an exemplary embodiment of the present invention.

In certain exemplary embodiment of a vascular graft, an electromechanical transducing material (e.g., a piezoelectric film, such as a PVDF film) is etched around the graft circumference in a circular to spiral pattern. Referring now to FIGS. 1 and 2, patterned electromechanical transducing films 12 are illustrated in planar form, prior to rolling into cylindrical form. The configurations illustrated not only improve flexibility, but also mimic the arrangement of SMCs in native arteries. Referring now to FIG. 3, segmenting the material 12 into lengths of a few hundred microns long by about ten microns (e.g., five to twenty microns) in diameter further simulates the dimensions of SMCs.

In another exemplary embodiment of a heart valve, a film of electromechanical transducing material is etched on the blood contacting surfaces of the valve leaflets in the axial and circumferential directions in a pattern that stimulates the natural arrangement of SMCs.

In accordance with certain other exemplary embodiments of the invention, a film of electromechanical transducing material is attached to the tissue-contacting surface of an implant. As noted above, the film may be patterned to facilitate bending and/or to mimic the arrangement of cells or structures of the native anatomy being replaced. Where the tissue contacting surface is a blood contacting surface, the film may be configured such that the blood-contacting surface becomes negatively charged during systole (in response to increasing blood pressure). In some instances, the internal resistance or shunt resistance of the film is selected to provide a high-pass filter time constant of about two (2) to one hundred (100) seconds, more typically between five (5) and ten (10) seconds. This allows diastolic to systolic changes in blood pressure to create a surface charge, while preventing slow changes in blood pressure or temperature from creating a surface charge.

One example of a beneficial film is a polyvinylidene fluoride (PVDF) copolymer, which is available from Measurement Specialties, Inc. located in Norristown, Pa. 19403, USA. This film can be provided in a variety of thicknesses, for example, a thickness in the range of 0.1 to 10 microns. Such a thickness range is expected to generate a surface charge density change from diastole to systole that is approximately the same as the surface charge density change estimated for the cell membrane of tissue underlying the endothelium in the native anatomy being replaced. Of course optimal thickness for a given application can be readily determined through suitable experimentation. Technical manuals describing the applications of these piezoelectric films can be obtained from Measurement Specialties, Inc. at www.msiusa.com.

Baro-electric stimulation (e.g., stimulation based on changes in surface charge which occur in response to changes in pressure) is expected to promote the adhesion and growth of ECs (i.e., healing) on the tissue contacting surfaces of the implant.

In some embodiments of the present invention, synthetic prostheses, for example, a vascular valve, is formed from the film, whereas in other embodiments, the film is adhered to the tissue contacting surface of a synthetic prosthesis, for example, a vascular graft, blood pump chamber, heart valve, venous valve, stent, blood filter, patch placed over infarcted heart tissue, and so forth.

Wound Healing Applications

In various embodiments of the invention, medical devices having at least one tissue contacting surface with a charged surface believed to provide one or more desirable effects including the attraction of ECs, the ability to provide an electrically compatible substrate, and the ability to provide an energy source to the endothelium at the margins of the implant which is believed to promote healing, among others.

Figure 4A:
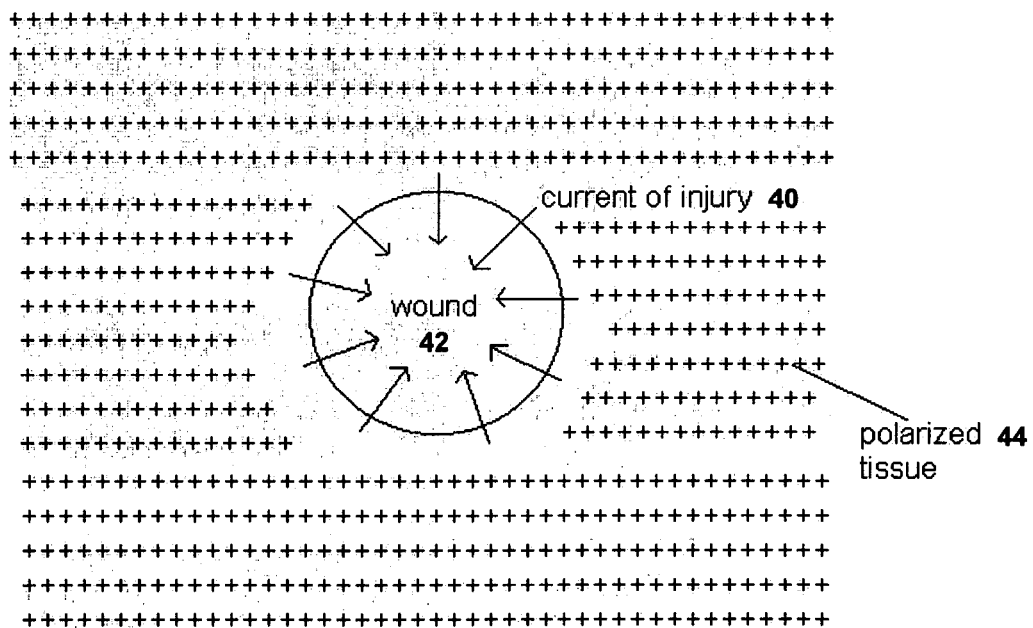
FIG. 4a is a schematic top view of a circular wound or dead tissue surrounded by healthy, positively polarized tissue, which shows the current of injury.

This latter process is illustrated in part by reference to FIG. 4a. The figure schematically illustrates normal polarizable tissue 44 having a positive charge, as typically found in the extra-cellular space. The circle represents a wounded or non-living region 42, which is uncharged. When the circular area is uncharged, positive charges on the margin of the circle are repelled inward toward the center of the circle by surrounding positive charges. In other words, an electric field is directed radially inward toward the center of the circle, and a so-called "current of injury" 40 flows inward from the margins. On the other hand, when the circle is filled in with positive charge (e.g., where the circle is occupied by healthy tissue), there is no lateral electric field and there is thus no preferential direction of current flow on the surface.

Figure 4B:
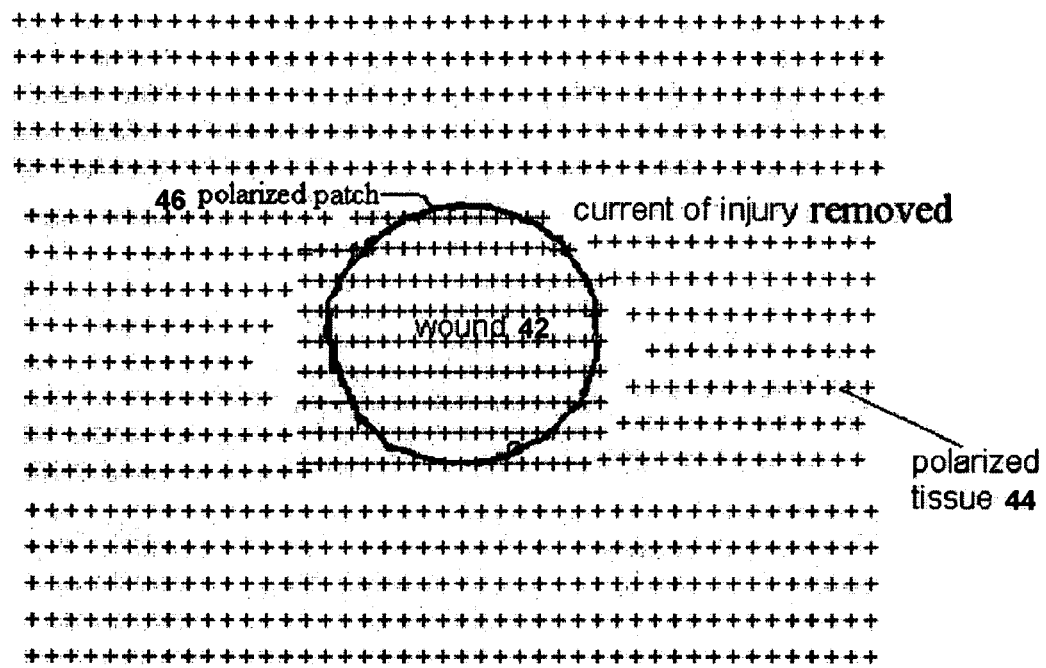
FIG. 4b is a schematic top view a polarized patch, according to an exemplary embodiment of the present invention, which is placed wounded tissue like that of FIG. 14a, removing the current of injury.

In one embodiment of this invention, a polarized patch 46 is placed over the wound area, as shown in FIG. 4b. The polarity of the patch 46 substantially matches the polarity of the surrounding tissue, so that minimal current of injury flows when the patch is in place. In FIG. 4b, the patch may represent, for example, the positive pole of a battery, or the positive surface of a polarized layer. If the polarity of the surrounding tissue changes with time, the polarity of the patch is changed to match the polarity of surrounding tissues to maintain a minimal current of injury.

Figure 17A:
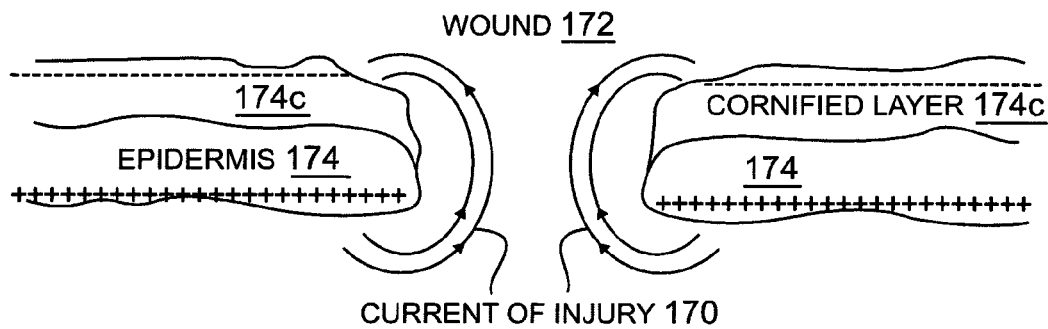
FIG. 17a is a schematic side view of the current of injury in a skin wound.

In the case of a wound in the skin 172, as schematically illustrated in FIG. 17a, the positive charge faces the extra-cellular space on the inside surface of the epidermis 174, which is maintained positive relative to the outside surface of the skin, associated with the cornified layer 174c, by ion pumps in the epithelium that supply energy on a continuous basis to maintain the charge separation. In this case, the charge is essentially non-phasic, and the injury current 170 is therefore a substantially d.c. current, returning to the negative outside surface as the current passes through the wound. Electric fields at the margin of wounds are on the order of 1 Volt/cm. It is known that wound healing can be accelerated when an electric field of this same order of magnitude is applied externally. This is typically achieved by placing the negative electrode of an external battery or power source at the center of the wound, with the positive electrode placed as a patch on the skin.

Although not wishing to be bound by theory, it may be presumed that the external field offloads the epithelial cells at the wound margin, which would normally supply the current of injury through internal cell energy driving the ion pump to maintain charge separation across the cell membrane. Since the current of injury is supplied by the applied electric field, these cells can then focus on mitosis and migration into non-endothelialized regions of the surface. Alternatively or additionally, the applied field may provide a definite signal and direction for epithelial cell migration into the wound. By generating an electric field that keeps the outside of the wound negative relative to the inside of the wound, the above effects are achieved.

Figure 16A:
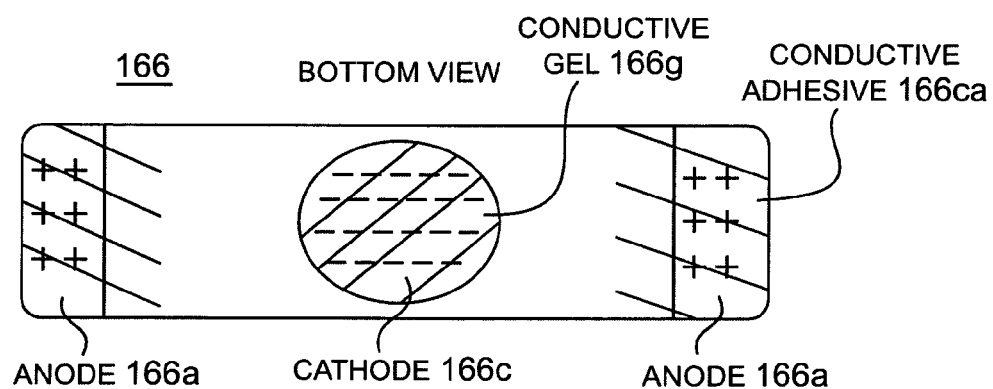
FIGS. 16a and 16b are schematic bottom and side views, respectively, of an electric bandage, according to an exemplary embodiment of the present invention.
Figure 16B:
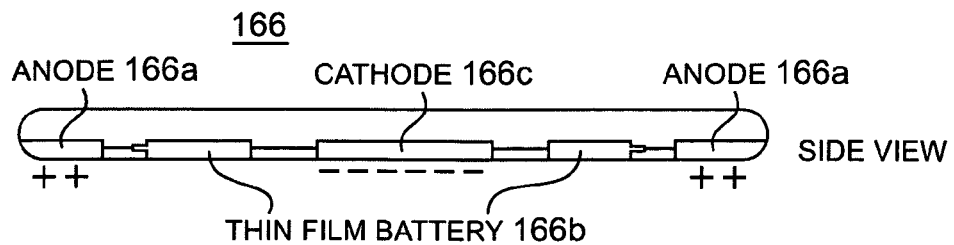

An example of a device for generating an electric field at the wound is illustrated in FIGS. 16a and 16b. The figure shows an "electric bandage" 166 driven by flexible thin-film dc batteries 166b (such as those available from Solicore, Inc., Lakeland, Fla. 33805, under the product name FLEXION) which can be embedded, for example, within the bandage material. (Of course, such a device can also be driven by other power sources including external power sources which may be coupled, for example, via conductors or via inductive or capacitive coupling, as well as power sources which provide the electric field with a phasic component, if desired.) The bandage 166 is further provided with a central cathode 166c, which is covered with a conductive gel 166g and peripheral anodes 166a which are covered by a conductive adhesive 166ca. Of course other configurations are possible, including circular bandages with a central circular cathode and a ring-shaped peripheral anode encircling the central cathode, among others.

Figure 17B:
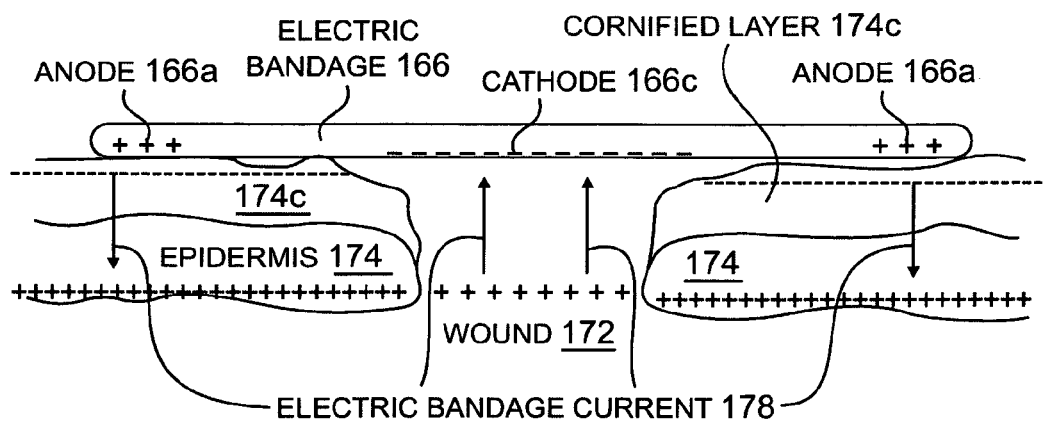
FIG. 17b is a schematic side view of the electric bandage like that of FIGS. 16a and 16b placed over a skin would like that of FIG. 17b.

When the bandage is placed over a wound and adhered to the skin as illustrated in FIG. 17b, a current flows 170 from the batteries 166b, through the anodes 166a at the ends of the bandage, through the conductive adhesive stripes 166ca, through the cornified layer 174c and epidermis 174, returning through the wound 172 and conductive gel 166g to the negative electrode (cathode 166c) in the center of the bandage. The gel 166g may additionally contain a therapeutic agent such as those that are known for use in bandages.

As shown in FIG. 17b, when the electric bandage 166 is in place, the outside of the wound 172 is charged negative, having the same charge as skin surrounding the wound. The return current fills the underside of the skin with positive charge, eliminating the injury current flowing from the epithelial cells and replacing it with current flowing from the bandage 166. It is also seen in the figure that the charge separation across the epidermis 174 provided by the battery 166 helps to maintain the skin potential, offloading the sodium pump mechanism, and therefore leaving the epithelial cells with more energy to be used for mitosis and migration. Experiments have revealed that epithelial cells migrate toward the negative pole in an applied electric field. Thus, the placement of the bandage cathode 166c over the wound 172 in FIG. 17b may also provide a signal to direct epithelium migration into the wound 172.

Experiments also suggest that electric stimulation of wound healing may be optimized if the stimulation current is reduced over time (period of days or weeks). In this regard, the batteries in the bandage may be chosen to have a lifetime that is commensurate with the desired application time to optimize healing. Some studies suggest that a reversal of the polarity of the stimulation current is desirable in the final phases of wound healing. Without wishing to be bound by theory, this effect presumably retards advancement of the epithelium in the final phase, to provide a controlled knitting of the wound margins without excessive scarring due to overproduction of cells.

Thus, in some embodiments, a phasic voltage is applied to the wound, with the charge applied to the outside surface of the wound going from zero to negative at the time of application, and falling to zero over time, or even becoming positive in the final phase before falling to zero. The duration of each phase is related to the time required for healing, which is related to the size of the wound, and thus to the size of the bandage, with larger bandages having longer duration of each phase. For example, the lifetime of the batteries may be chosen to determine the length of each phase. Moreover, a higher voltage battery with negative polarity at the central patch may be placed in parallel with a discharged positive polarity battery of lower voltage. During the discharge phase of the negative battery, the positive battery is being charged. Batteries may be designed to have a rapid fall off of voltage to zero, so that when the negative battery voltage drops below the positive battery voltage, the positive cells begin their life span as the negative cells are ending theirs. Of course an electronic circuit (e.g., within the bandage or external to the bandage), could control battery voltage versus time according to essentially any programmed phasic relationship.

Alternatively, a sensor may be placed within the bandage to detect the progress of wound healing, and the sensor signal may be used to control the duration of each phase of stimulation. In a rudimentary embodiment, the sensor may simply measure impedance (or resistance, where a d.c. signal is used) of the skin between the cathode and anodes of the bandage, which is expected to fall as the wound heals. For instance, an electronic circuit external to or within the bandage can measure the impedance, and reduce the bandage voltage to zero or a positive value when the impedance drops below a set value. In the latter case, the positive bandage voltage is further reduced to zero when the impedance drops below a second, smaller value.

Myocardial Infarct Patch

In another example, the circle in FIG. 4a may represent a region of myocardial infarction in the wall of the heart. In this case, however, the charge is phasic, and is believed to alternate from positive to neutral or negative as the heart depolarizes on every beat. The current of injury is therefore also phasic and synchronized with the changes in the electric potential of the heart, which may be seen on ECG (electrocardiogram) tracings as an S-T segment elevation.

As a specific example of the present invention, an electromechanical transducing (e.g., piezoelectric or electrostrictive) film patch 186 can be applied to an area of injury corresponding to phasic tissue, for example to an infarcted region of the heart 182, as illustrated in FIGS. 18a and 18b. The patch 186 can be, for example, sutured to healthy tissues on the margin of the infarct, with the stresses that are applied to the piezoelectric or electrostrictive film as the heart contracts and relaxes being used to produce patch membrane voltages that can be in a phase relationship with voltages in surrounding tissue to promote healing. For example, if the film polarizes in synchrony with surrounding tissues, the circle in FIG. 4a is filled with positive charge from the patch. The current of injury is thus reduced or eliminated, and the ECs at the margin of the infarct are off-loaded, which is expected to allow theses cells to focus on promoting in-growth into the infarct region to cover and heal the patched area.

FIGS. 18a and 18b show patches 186 on both the endocardial and epicardial surfaces of ventricle wall 184 of the heart in the infarct area 182. When the surrounding tissue 184 is polarized, as in FIG. 18b, sodium and calcium are driven out of the myocardial cells to generate a positive charge on the exterior surfaces. As the heart contracts, a wave of de-polarization is propagated through the myocardium, during which time gates open in myocardial cells, allowing both sodium and calcium to enter the cells, with a smaller concentration of potassium leaving the cells. During the de-polarization phase, the exterior surfaces of the ventricle wall 184 may be neutral, or even negatively charged relative to the interior of the wall 184, as shown in FIG. 18a. Generally, myocardium is depolarized during the S-T segment of the electrocardiogram, and polarized during the T-P segment, with atrial tissue depolarized during the P-Q segment. However, the depolarization wave front reaches a given region of myocardial cells at a specific time during the heart cycle. Thus, the phasic charge on the myocardial patches shown in FIGS. 18a and 18b may be obtained by synchronizing the application of charge with a local measurement of the ECG signal. Hence, the patches 186 may be simple electromechanical transducing materials with stretch induced charge, or alternatively, they may be more complex structures which sense a local signal and actively control surface charge, for example, using embedded ECG-type sensors to control an internal battery via embedded electronic circuitry. In this regard, a myocardial patch may provide a phasic current of injury (rather than phasic surface charge) using an electric bandage analogous to FIG. 17b. The phasic current may alternatively be provided by a first electrode placed on or within the zone of infarction, and a second electrode placed on or within surrounding healthy myocardium.

Vascular Prostheses

In a third example, the circle in FIG. 4a represents a non-living synthetic implant surrounded by normal vascular endothelium. The implant may be a vascular graft, heart valve, or any other blood-contacting prosthesis in contact with polarizable tissues such as cardiovascular endothelium. To reduce or eliminate the current of injury flowing from ECs at the margin of the implant, the synthetic surface can be stimulated so that its surface charge approximates the sign and magnitude of neighboring tissue.

The surface charge on vascular endothelium is influenced by the presence of charged entities such as a surface glycocalyx or negatively charged protein groups fixed to the EC surface, as shown schematically in FIGS. 19a and 19b. The EC membrane tends to depolarize during systole, as illustrated in FIG. 19b, although not enough to cause an action potential and depolarization wave. Rather, charge passes through the membrane, reducing the membrane potential, in response to the rise in blood pressure. In this sense, vascular endothelium responds to local pressure variations in a manner analogous to electromechanical transducing materials, such as piezoelectric and electrostrictive materials. Because the glycocalyx 195 has a fixed negative charge, the effect of the partial depolarization is to render the endothelial surface overall more negative during systole when the positive surface membrane charge is reduced in magnitude.

Figure 20A:
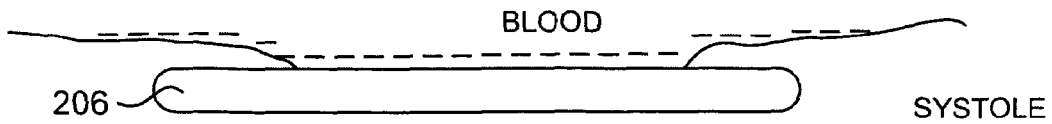
FIGS. 20a and 20b are schematic drawings illustrating a stimulated synthetic, blood-contacting surface, during systole and diastole, respectively, according to an exemplary embodiment of the present invention.
Figure 20B:
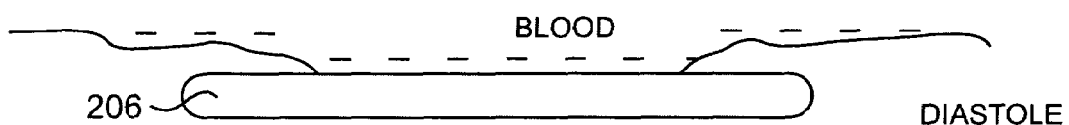

To mimic surrounding endothelium, a synthetic implant 206 is stimulated as shown in FIGS. 20a and 20b, with its surface charge more negative during systole, and less negative during diastole. Again, the polarization is assumed to be phasic, varying in synchrony with blood pressure or cardiac depolarization. The injury current flowing from the native tissue into the implant region is thereby reduced or eliminated, promoting in-growth of ECs. Alternatively, the current of injury may be supplied by a battery or other energy source in analogy to the electric bandage of FIG. 17b. In this case a first electrode would contact native tissue at the ends of the graft, and bare surface of the graft would comprise a second electrode. Again the surface would have a fixed negative charge. During systole, current would flow from the ends of the graft inward, providing the current of injury. During diastole, the current would be diminished, reduced to zero, or even have reversed polarity.

Whether the mechanism of healing is directed to migration of ECs, off-loading of the injury current from cells at the margin of the implant, or the supply of electrical energy to these cells, the need for a phasic variation in implant surface charge is addressed by the present invention. While it is presently believed that implant surface charge variations should be in phase with the polarization of surrounding tissues, alternative phasic relationships may better stimulate healing and are within the scope of the present invention.

For example, studies of cell migration in d.c. electric fields have shown that some cells migrate toward the negative pole of an electric field, while others migrate toward the positive pole. Even variations of the same cell type, for example, arterial endothelium versus venous endothelium, may migrate toward opposite poles of an electric field. Thus, the optimal surface charge stimulation to promote growth of venous endothelium may be 180° out of phase with that required for arterial endothelium, or out of phase by some other increment. In addition, different physiologic signals, for example pressure and ECG may be out of phase or have a complex phase relationship, so that the optimal phase for stimulation may differ for different signal inputs. Even the same signal, such as blood pressure, may vary in magnitude and wave shape depending upon where it is measured in the body, e.g. arterial versus venous pressure.

Figure 21:
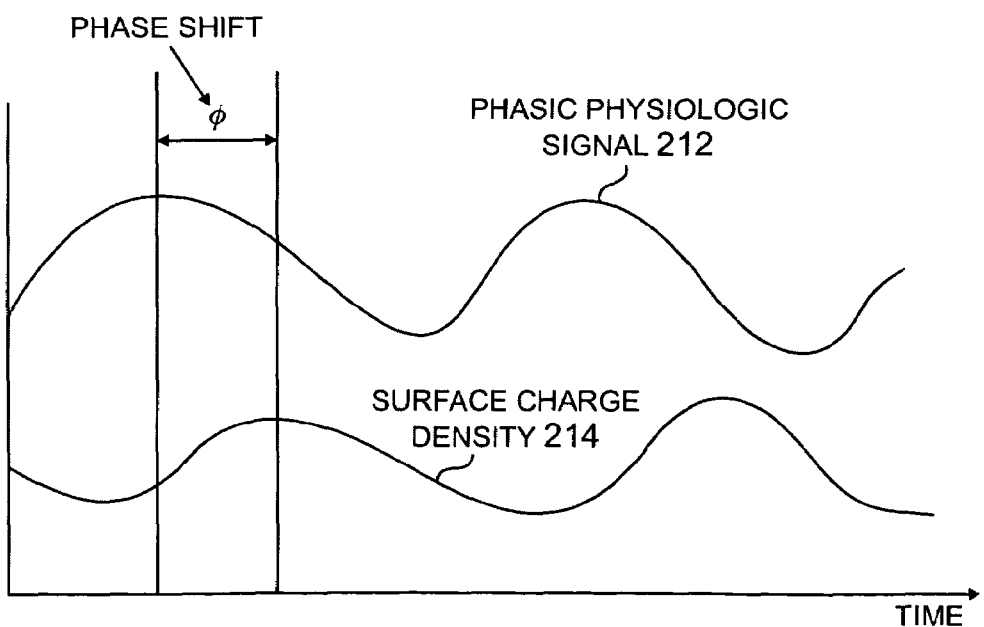
FIG. 21 illustrates surface charge density in a phase shifted relationship relative to a physiologic control signal.

This is illustrated in FIG. 21, in which the phase shift, Φ, between stimulation surface charge and a physiologic signal 212 is about +90°. The optimum phase relationship between surface charge and a native physiologic signal such as blood pressure, according to this invention, may be in the range from −180 degrees to +180 degrees. The physiologic signal may be, for example, blood pressure, blood flow velocity, local ECG signal, shear stress at the implant wall, or other suitable physiologic signal. More complex phase relationships may be preferred in some tissue settings. For example, non-linear dependence of surface charge amplitude and/or surface charge phase on phasic signal amplitude and phase may be implemented.

It has long been recognized that vascular ECs can migrate through a porous implant surface, beginning as endothelial buds on the outside graft surface that migrate through the pores in the form of capillaries, and then spread over the blood-contacting surface. In this regard, in some aspects of the invention, electrical stimulation may be applied across the body of a porous region, such as a porous graft, to promote EC migration into the graft from tissues outside the graft. This is illustrated schematically in FIG. 22b. (Surface stimulation by a phasic voltage is again illustrated in FIG. 22a, and contrasted to stimulation across the body of a porous graft in FIG. 22b.)

As in other embodiments of the invention where an endogenous energy source is available (e.g., pressure), the voltage in the various vascular prostheses of the invention may be applied passively or actively in response to a physiologic input. For example, FIGS. 22a and 22b illustrate capacitive charging across the film and substrate surfaces, respectively, which can either be applied actively or by using a material which causes charge separation in response to an endogenous signal (e.g., using a piezoelectric material).

Figure 23A:
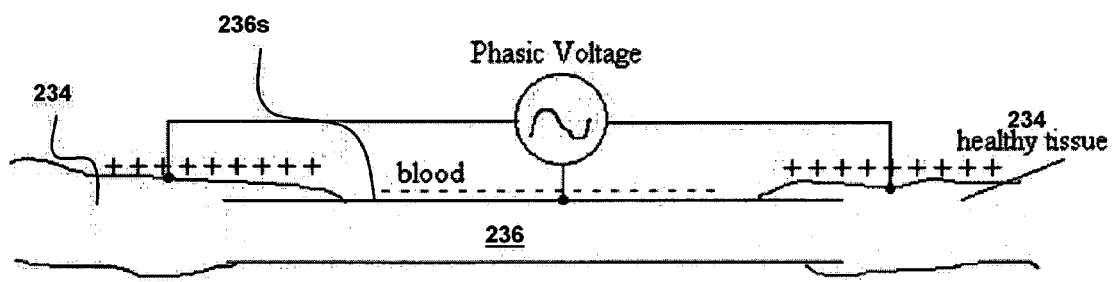
FIG. 23a is a schematic drawing that depicts stimulation voltage applied between an implant surface and adjacent tissue, according to an exemplary embodiment of the present invention.
Figure 23B:
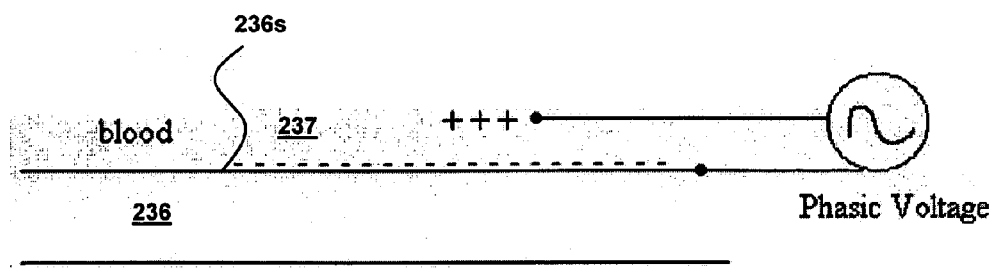
FIG. 23b is a schematic drawing that depicts stimulation voltage applied between a blood-contacting implant surface and adjacent blood, according to an exemplary embodiment of the present invention.

It is also known that progenitor cells found in blood may deposit on an implant surface, and differentiate into various useful cell types, such as fibroblasts, SMCs, or ECs, which may heal a surface under proper conditions. Stimulating capture of progenitor cells by the supply of a voltage between the blood and the implant surface is yet another aspect of this invention. FIGS. 23a and 23b illustrate embodiments of this invention in which a phasic voltage is applied (e.g., via conductive coupling) such that a phasic current flows: between the surface 236s of the implant 236 (which may be a tubular implant, such as graft, in these embodiments) and neighboring endothelium 234 in FIG. 23a; and between the implant surface 236s and the blood 237 in FIG. 23b.

Figure 22A:
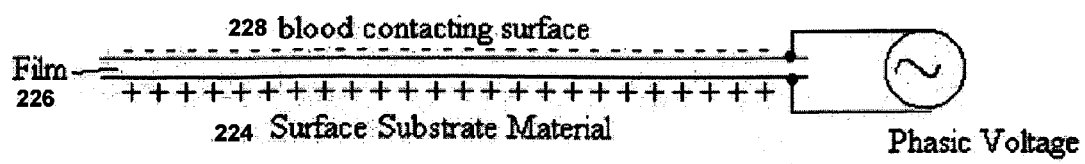
FIG. 22a is a schematic drawing that depicts charge separation across a film attached to an implant surface, according to an exemplary embodiment of the present invention.
Figure 22B:
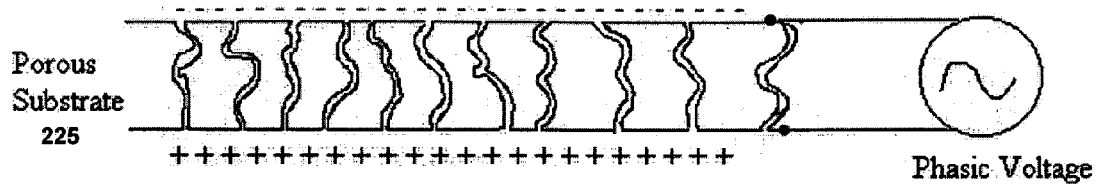
FIG. 22b is a schematic drawing that depicts charge separation across the body of a porous implant, according to an exemplary embodiment of the present invention.

Hence, FIGS. 22a through 23b represent four modes of surface stimulation, any one or any combination of which may be used to stimulate healing of an implant surface. In FIG. 22a a charge separation is created at the implant surface by actively or passively providing a voltage across a film layer 226, for example, to simulate the membrane potential of vascular ECs or SMCs, so as to attract and/or stimulate the ingrowth of neighboring ECs to heal the surface. In FIG. 22b, a phasic voltage is actively or passively applied across the surface of a porous implant, for example, to stimulate the ingrowth of ECs through the pores to cover the blood-contacting surface of the implant. In FIG. 23a, a phasic voltage is applied between the graft surface and neighboring healthy endothelium, in analogy to the electric bandage of FIG. 17b. Finally, in FIG. 23b, a voltage is applied between the graft surface and the neighboring blood, for example, to stimulate the capture of progenitor cells that will lead to surface healing. In the modes such as those of FIGS. 23a and 23b, in which current flows through tissue or blood, steps may be taken to prevent electrode fouling. Antifouling measures include the use of ionic electrodes, such as silver-chloride, and the use of anti-inflammatory-drug-eluting electrodes, such as the steroid eluting electrodes employed in the pacemaker industry.

Tissue Growth Deterrence

According to another aspect of the invention, phasic variations in surface charge (for, example out of phase with surrounding tissues) may be applied in order to deter, rather than promote, tissue in-growth. For example, as noted above, cells may be classified based upon their tendencies to migrate toward or away from the negative pole of an electric field. For instance, arterial vascular ECs are known to migrate toward the negative pole of an electric field, and away from the positive pole. In some embodiments, in order to inhibit tissue growth, a surface stimulation that promotes healing or endothelialization is advanced or retarded by 180°, or the amplitude of the surface stimulation charge is reversed in polarity. An implant that deters tissue growth may be used, for example, to prevent restenosis (which is associated with undesirable proliferation of cells such as SMCs, commonly following vascular injury such as that associated with PTCA) or to prevent the growth of unwanted tissues, for example, tumor blood vessels or tumor cells. Each cell type may have a specific stimulation waveform that inhibits advancement of cells, which can be optimized experimentally.

Configuration of Electrical Elements

In order to provide a charged tissue contacting surface, the devices of the present invention are typically provided with one or more electrical elements, such as conductors (e.g., metals, conductive polymers, etc.), electromechanical transducing materials (e.g., piezoelectric materials, electrostrictive materials, etc.), and so forth. The electrical elements can be incorporated within the device or applied to an external surface of the device. In aspects where electrical conductors are employed, they may be conductively, capacitively or inductively coupled to a source of electrical energy.

According to various aspects of the present invention, electrodes, or electrically conducting elements, are embedded within the materials at the implant surface to provide the desired surface charge. Consequently, the electrodes are insulated from each other from contact with conductive tissue or blood as well. Such electrodes can be provided in various forms, including filaments (which may be knitted or woven) and films (which may be patterned) to improve device flexibility. They can be formed from various materials, including metals, conductive polymers, and so forth.

FIGS. 24a to 24d illustrate conductors 244 having various shapes, which are provided on the surface of a tubular medical device 242 and covered with an optional insulating layer of material 246, for example, an insulating polymer such as polyethylene or polytetrafluoroethylene (e.g. TEFLON), among others. As noted above, these embodiments may utilize any electrically conductive material to transfer charge or electrically couple various components or regions, and the electrical conductors can be provided in various forms, including the form of conductive wires or fibers as shown. The electrical conductors can be incorporated within the device (e.g., by embedding them within the device surface as illustrated in the right-hand portions of FIGS. 24a-d), or applied to an external surface of the device (e.g., as illustrated in the left-hand portions of FIGS. 24a-d), in which case the conductors may be optionally coated with a layer of insulating material, for instance, an insulating polymer such as polyimide or polyurethane, among others.

Figure 24A:
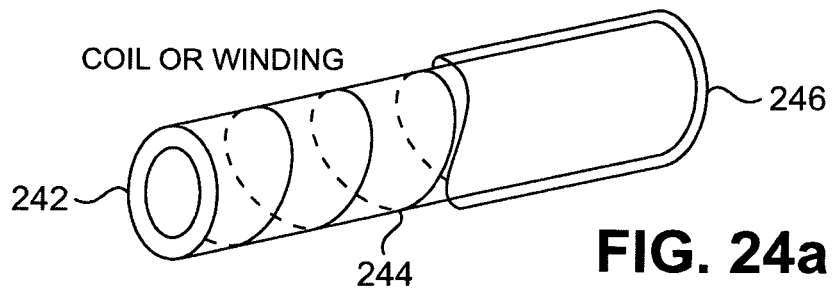
FIG. 24a through 24d are schematic drawings showing stimulation wires embedded into a surface, in accordance with four exemplary embodiments of the present invention.
Figure 24B:
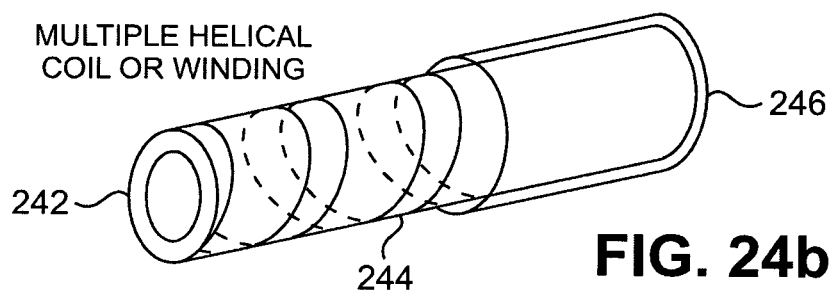
Figure 24C:
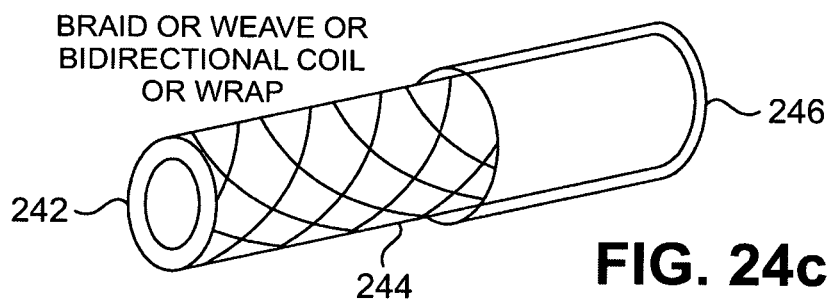
Figure 24D:
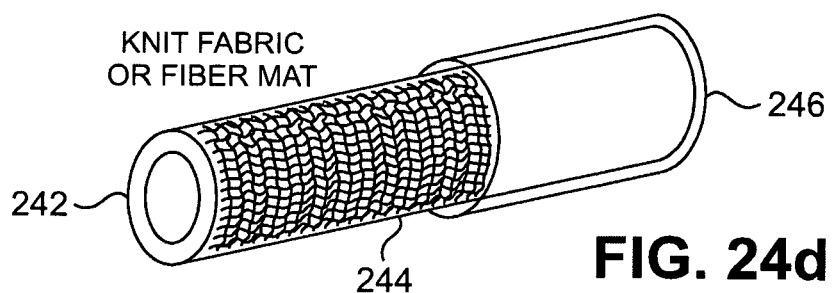

Several specific conductor 244 configurations are illustrated in FIGS. 24a to 24d, which show a single helix wire coil (FIG. 24a), a double helix wire coil (FIG. 24b), woven conducting filaments (FIG. 24c), and knitted conducting filaments (FIG. 24d). The conductor 244 can be located at a surface of the device (as illustrated in the left-hand portions), or can be located within the body of the device (not illustrated), or within or beneath layers such as the optional layer 246 shown on the right-and portion of each device 242. Regardless of the exact location, the conductors 244 illustrated are sufficiently proximate the tissue contacting surfaces of the devices 242 so as to readily influence surface charge at the same.

These figures show a tubular device 242, but the conductor configurations clearly apply to devices of other shapes as well, such as rods, sheets, membranes, rings, and so forth.

FIGS. 25a-25i each schematically illustrates a portion of a device 252 having a film 254 of material facilitating electrical enhancement of tissue response of the present invention Various configurations are illustrated; as elsewhere herein, these are meant as examples, and the inventive devices and methods are not limited to these examples. Any of the embodiments described herein may utilize an electrically active film, for example, a transducing film such as an electromechanical transducing film (e.g., a piezoelectric or electrically restrictive film which generate an electric charge in response to deformation) or a conducting film (e.g., to transfer charge or electrically couple components or regions). The film can be configured as a complete layer, or a porous layer, or can be configured with various intermittent shapes or patterns. For example, a pattern of lines, grids, dots, diamonds, rings, and so forth may be utilized. Various discrete regions may incorporate different electrical stimulation to enhance tissue response in a different manner as is appropriate to the location and application. For example, a vascular graft may have one or more portions where EC proliferation or migration is enhanced, and/or one or more portions where SMC proliferation or migration is reduced, and/or one or more portions where inflammatory cells are inhibited, and/or one or more portions where stem cells are attracted or stimulated, and so forth. An occlusive device may have anchoring portions where proliferation of fibrous tissue is enhanced to provide rapid and secure anchoring or sealing.

Figure 25A:
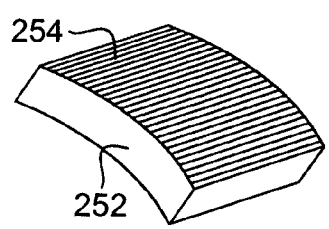
FIGS. 25a through 25i are schematic drawings that illustrate various patterns of metal film for stimulation in accordance with various exemplary embodiments of the present invention.
Figure 25B:
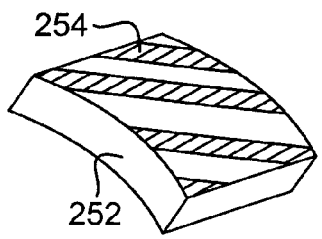
Figure 25C:
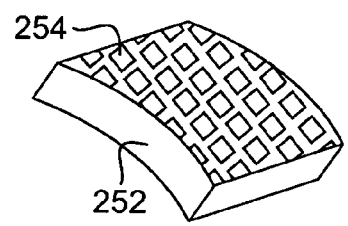
Figure 25D:
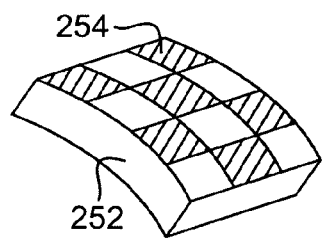
Figure 25E:
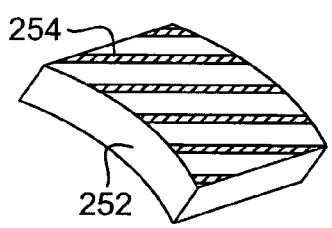
Figure 25F:
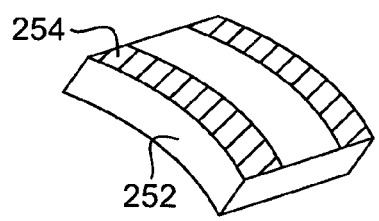
Figure 25G:
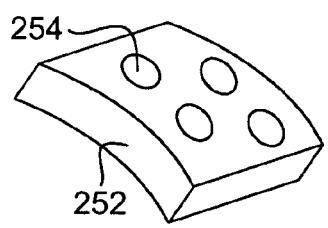
Figure 25H:
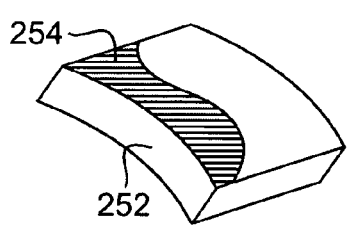
Figure 25I:
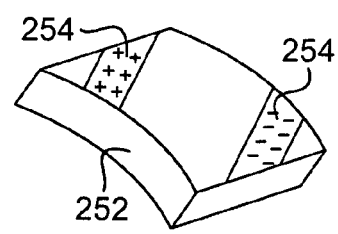

FIGS. 25a-25i, each illustrates a substrate 252, over which is provided an electrically active layer 254, which may be solid or porous. Layer 254 is illustrated in a variety of configurations, including the following; a complete layer (FIG. 25a), a film patterned in the form of stripes (FIG. 25b), a film patterned in the form of a diamond grid (FIG. 25c), film patterned in the form of a checkerboard (FIG. 25d), a film having stripes of alternating polarity (FIG. 25e), a film with end portions stimulated (FIG. 25f), a film having a dot pattern (FIG. 25g), an arbitrary shape of film (FIG. 25h), and stimulated zones of differing voltage and polarity (FIG. 25i). The voltage, polarity, periodicity, and/or phase may vary at different locations on the film to achieve the desired tissue stimulation at various regions of the device.

Sensors

In some embodiments, implanted sensors are provided which can measure a phasic parameter, such as blood pressure, blood flow, or an electrocardiogram signal, and an implanted power source delivers charges of opposite polarity to two implanted electrodes, making one surface positively charged and other negatively charged. The tissue-contacting surface of the implant can be charged positive, negative or neutral in response to the sensed physiologic parameter.

An external or embedded computer chip may be employed to control the stimulation sequence as a function of sensed inputs. Sensors may also be included as previously noted to monitor the healing process (or lack thereof), in which case the electrical stimulation sequence can then be automatically altered on the basis of the input from the sensors. Alternatively, a physician can alter the stimulation sequence, for example, in the case of an embedded computer chip, by reprogramming of the computer chip via r.f. signals transmitted to the computer from outside the body. For example, surface stimulation may only be desired until the tissue-contacting surface heals, which may take weeks or a few months after implantation. Healing may be sensed, for example, by local sensors, and the stimulation modified or discontinued automatically or on a command from the physician. As another example, energizing the implant surface for only part of each day may be sufficient to promote healing, and doing so would conserve the stimulation energy source.

Energy Sources

Figure 26A:
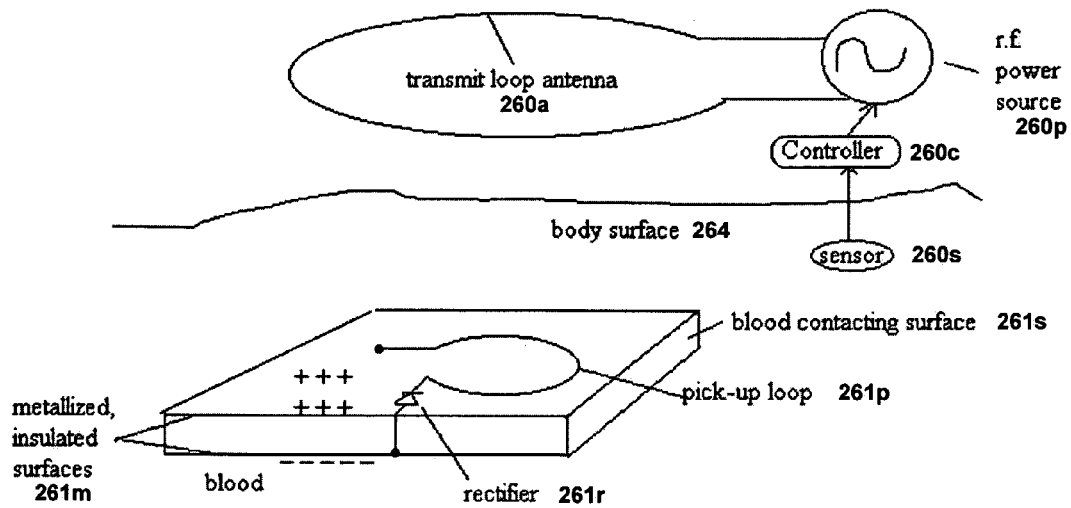
FIGS. 26a and 26b are schematic drawings that show inductive coupling of stimulation energy to implanted medical devices, according to two exemplary embodiments of the present invention.

Electrical energy to power an implanted or inserted device can be derived conductively from leads that exit the body through the skin, with the patient carrying a small power source until healing is complete. Or power can be inductively coupled into the body to recharge a storage device such as a battery or to charge an implanted capacitor. FIG. 26a shows an embodiment in which power is transmitted from an r.f. power source 260p, through the body surface 264, and to a pick-up loop 260a located within the body. The r.f. transmit power is modulated by a control unit 260c that responds to a sensed physiologic input using sensor 260s. The control unit 260c and antenna 260a are shown external to the patient body, however, they can also be implanted. The transmitted r.f. electromagnetic field induces a current in a pick-up coil 261p, which is located on the implant surface 261s, but which could also be located within the implant surface or remote from the implant surface. The current is rectified, for example using a diode as a rectifier 261r, such that conductive films 261m on opposite facing surfaces of the implant have opposite charges. The current could equally well be applied to any of a variety of stimulation modes, including those described conjunction with FIGS. 22a through 23b.

Alternatively, the induced current could charge a storage capacitor or battery, and a sensor and controller located on the implant itself could control delivery of stimulation charge.

Figure 26B:
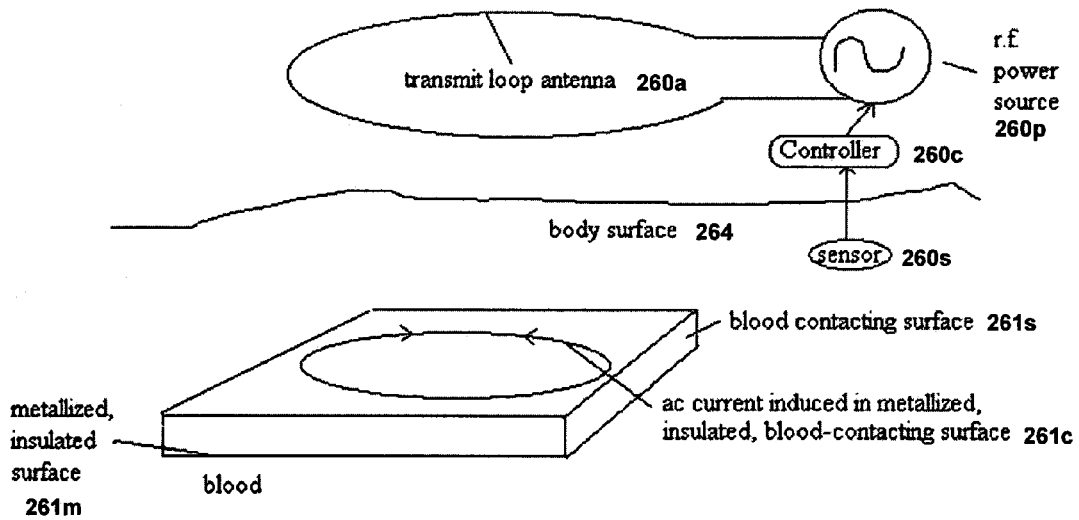

The r.f. transmit coil of FIG. 26a may alternatively be used to directly induce, through the body surface 264, a.c. currents 261c in a metallized, insulated, blood-contacting surface 267, as shown in FIG. 26b. Induced currents are typically alternating, with frequency equal to the external drive frequency, and a.c. currents may promote healing in some applications. Phasic stimulation is achieved by modulation of the amplitude of the r.f. antenna current as a function of time. For example, the r.f. current 261c may be turned on during systole, and turned off during diastole, using, for instance, ECG, blood pressure or other signal, which is sensed by sensor 260s and used by the controller 260c to synchronize the ON and OFF times. The r.f. antenna 260a and power source 260p may be external to the body as shown in FIG. 26b, or may be implanted. Stimulation via magnetic induction may be utilized in any of the application areas discussed herein. The metallized surfaces may be patterned or wire-wound to customize the zones of stimulation.

Figure 26C:
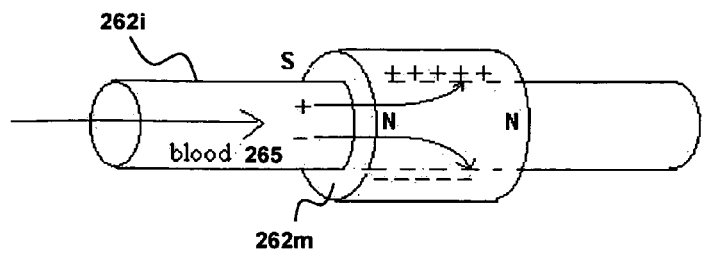
FIG. 26c is a schematic drawing that illustrates magnetic separation of ions in the blood to charge an implant surface in accordance with an embodiment of the present invention.

Another, passive approach to charging an implant surface is shown in FIG. 26c. In accordance with an electromagnetic embodiment of the present invention, a permanent magnet 262m is implanted surrounding the implant 262i. The Hall effect then causes ions in the blood 265 flowing through the magnet to be deflected to charge opposing sides of the implant. The surface charge density is proportional to the velocity of blood flow in the Hall effect. Thus, the phasic change in blood velocity causes a phasic stimulation of the surface charge on the implant blood-contacting surface.

Figure 26D:
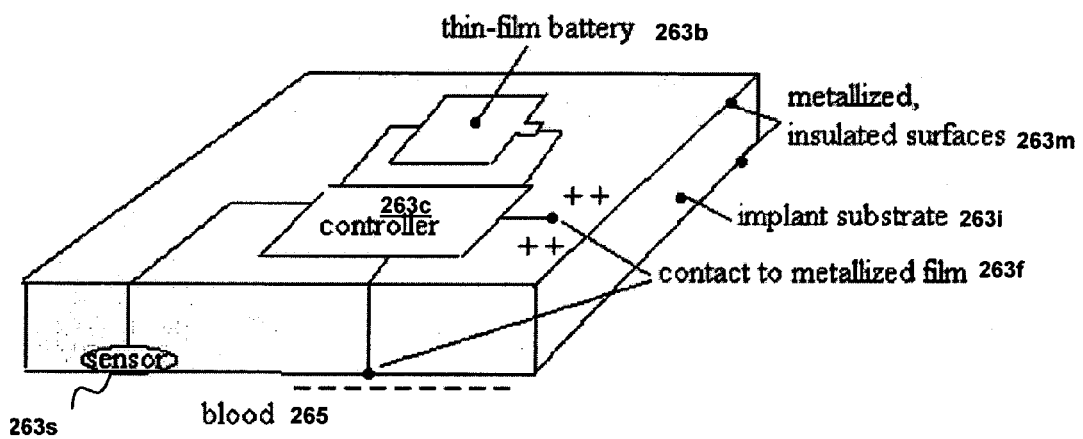
FIG. 26d is a schematic drawing that shows implant surface charging using an implanted, thin-film battery for power, according to an exemplary embodiment of the present invention.

In yet another embodiment illustrating stimulation power, FIG. 26d shows a thin-film battery 263b powering a sensor 263s and controller 263c and supplying stimulation charge to metallized films 263m on opposite faces of the implant substrate 263i via film contacts 263f, all as components of the implant surface in the embodiment shown. The lifetime of the battery may be designed to coincide with the desired period of surface stimulation, or the battery can be recharged as needed, for example using an inductive coupling scheme such as is illustrated in FIG. 26a.

As yet another power option, an electromechanical transducing film (e.g., a piezoelectric film) may be used where body-generated mechanical forces are generated at the site of device administration which are sufficient to deform the film and thereby achieve charge separation. For example, the film can be attached to the beating heart or exposed to blood pressure to provide electrical energy for the implanted stimulation electrodes and controller.

Phasic Stimulation

As noted above, the optimum stimulation sequence may be different for different tissue. For example, peripheral arteries are perfused during systole, while coronary arteries are perfused during diastole (because the heart squeezes off the distal coronary arterioles during systole). Thus, the optimum stimulation sequence may be different for coronary and peripheral arteries. As another example, some types of smooth muscle have a self regulated rate of change of membrane potential caused by slow leakage of Ca++ ions into the cells until the membrane is sufficiently depolarized to generate an action potential, causing contraction, followed by repolarization. Contraction rates for these so-called "pacemaker waves" may be on the order of seconds to tens of seconds.

In many embodiments, the optimal stimulation is expected to be synchronized with the natural phasic behavior experienced by the tissue of interest.

Moreover, an offset (e.g., in time or voltage) may be introduced to generate alternative stimulation waveforms. A charge offset may be introduced electrically or simply by selecting an implant surface coating that acquires the desired fixed charge upon hydration by the blood. Such coatings may contain glycoproteins or other proton donors that become negatively changed when hydrated. Electronegativity can also be achieved using carbon coatings or carbon containing materials such as carbon impregnated ePTFE. Simple and complex stimulation waveforms can be readily conceived and employed as stimulation sequences.

Hence, electrical stimulation waveforms for the practice of the invention may be simple or complex, and may be controlled by a signal that is periodic with the heart rate (e.g., blood pressure or electrocardial signal) or by asynchronous inputs. Control elements can be added to the implant that may or may not respond to physiological inputs. Waveforms may be selected to promote cell growth and healing, or to prevent the growth and migration of undesirable cells.

Although passive electromechanical transducing (e.g., piezoelectric or electrostrictive) films have limited inherent waveforms, e.g., negative charge during systole or positive charge during systole or vice versa. Adding a fixed offset voltage to the films would nonetheless expand the waveform options that are available. For example, if the tissue-contacting surface has a nominal positive charge, then it can become less positive under pressure. This adds the possibility of achieving a negative, neutral or positive surface charge during diastole.

In various aspects of the present invention, electrical stimulation of implant surfaces is employed as a technique to mimic the natural environment experienced by cardiovascular endothelium. For example, SMCs underlying endothelium can change their membrane potential in response to an increase in blood pressure, and this electrical response can be mirrored as a partial depolarization of the EC membrane. The SMC layer can therefore have a phasic variation in membrane potential as the pressure rises and falls during systole and diastole. Stimulation of a synthetic surface will mimic the electrical environment of the SMC layer if the synthetic surface is charged negatively during systole and is charged less negatively, or uncharged, or even positively charged during diastole. The stimulation is expected to encourage growth of an EC layer on the implanted surface, and provide electrical energy to the ECs. Phasic stimulation of the implant surface is therefore employed in some embodiments of the invention described herein, including simple or complex stimulation waveforms that may or may not be synchronized with the heartbeat. In certain embodiments, the optimal stimulation parameters are such that they simulate the electrical environment of tissues underlying the native endothelium. In such applications, surface stimulation may be provided temporarily or indefinitely, as will be the case with piezoelectric surface films.

Figure 27:
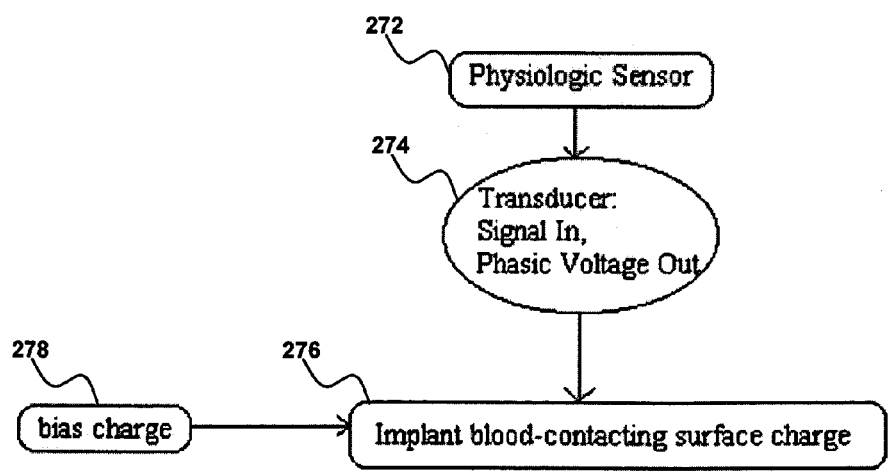
FIG. 27 is a generic block-diagram depicting surface stimulation, according to an exemplary embodiment of the present invention.

Various embodiments of surface stimulation will now be summarized using FIG. 27. A transducer 274 converts a physiologic signal to a phasic voltage that is applied to the blood contacting surface 276, generating a surface charge. A d.c. (non-phasic) bias surface charge 278 may also be supplied. In the case of a piezoelectric film, the film itself acts as both the sensor 272 and the transducer 274, converting blood pressure to surface charge. A bias 278 may be provided, for example, application of a voltage from a power source or by a surface treatment that results in positive or negative surface charge groups when the surface is hydrated by the blood. For example, surfaces or surface coatings containing phosphate or hydroxyl groups that are rigidly bound to the surface may hydrate in blood to form bound negative phosphate or hydroxyl ions. Large molecules or particles having multiple surface charges upon hydration are referred to as macro-ions. Macro-ions bound to the surface of an implant may render that surface charged when it is in contact with blood or other ionic body fluids.

Electromechanical Stimulation in Further Detail

Various approaches described herein that involve the use of electromechanical transducing materials (e.g., piezoelectric or electrostrictive materials), for example, by applying a thin film of piezoelectric polymer to tissue-contacting surfaces of medical devices, are potentially advantageous due to their simplicity of operation. In these embodiments, phasic variations in pressure (e.g., arterial blood pressure) could be used to generate phasic variations in surface charge. Specifically, if the piezoelectric film is polarized with its tissue-contacting surface negative, the negative surface charge will be generated when blood pressure rises during systole. Since piezoelectric films typically discharge over time periods that are shorter than intervals between the human heartbeats, the surface charge will be zero during diastole (which defines the baseline "DC" bias level of blood pressure).

The following discussion reviews the interaction of ECs with other cells and charged surfaces. Moreover, the properties of piezoelectric films are discussed and sample calculations of voltage and charge changes with pressure are presented. Although not wishing to be limited to a particular theory of operation, the following discussion suggests that creating a phasic charge density comparable to the change in SMC charge density in humans is achievable.

A brief review of the response of a cell membrane potential to pressure and charge is provided herein. A membrane potential of a cell is typically reduced in magnitude when the cell is exposed to increased fluid pressure. Thus, the membranes of both SMCs and ECs tend to depolarize with increasing blood pressure (e.g., during systole). An SMC will contract if the increase in blood pressure is sustained until the membrane is depolarized sufficiently to open voltage regulated $Ca^{++}$ channels. Phasic membrane potential changes, however, may occur without generation of action potentials that cause contraction.

Exposure to electrical charges affects cells though the action of the surrounding ionic fluid. For example, consider two neighboring cells separated by an ionic fluid (e.g., blood). If the membrane potential of one cell increases in magnitude, negative ions will be drawn from the intervening fluid towards the more positive outside surface of this cell membrane. This leaves the intervening fluid with a net increase in positive ions, which increases the membrane potential of the second cell. Thus, changes in membrane potential of cells are mirrored in neighboring cells. For example, changes in SMC membrane potential are propagated to ECs (and vice versa) through gap junctions, and this effect may be electrochemical in nature. The natural substrate for endothelium in arteries, i.e., the smooth muscle cell layer, depolarizes with increasing pressure, and the endothelial cell layer responds by also depolarizing.

Membrane potentials are also affected by the mere proximity of a neighboring cell which can be due, for example, to interaction, through the ionic medium of the negatively charged surface glycocalyx of neighboring cells. While the membrane dipole layer is overall electrically neutral, the fixed negative charges of the cell surface, such as those provided by the glycocalyx, renders the cell surface charge negative overall. This means that the ionic fluid in the neighborhood of the cell has an excess of positive ions that balance the glycocalyx negative charge. As cells approach one another, the overall concentration of positive ions in the intervening space is increased, thus increasing the membrane potential of both cells.

The situation is reversed when the cell is exposed to the negatively charged surface of a piezoelectric film. In this case, the negative charge on the film is balanced by the positive charge on the opposite surface of the film. The ionic fluid is overall electrically neutral, however, in close proximity to the negative surface, positive ions in the fluid will be attracted towards the negative surface and away from any proximate cell. Thus the magnitude of the neighboring cell membrane potential is reduced (depolarization) when it is exposed to the negative surface of a piezoelectric film. The tissue-contacting surface of the film may be negatively biased during manufacture (referred to as the poling process). Consequently, the surface becomes negatively charged when strained, for example, due to the application of pressure, as discussed in detail below. The increase in pressure during systole then tends to depolarize ECs adjacent the surface. This is simulates the effect experienced by ECs adjacent to the SMC layer in normal arteries.

Piezoelectric films are used in numerous applications as sensors and actuators. Piezoelectric film is prepared by stretching the film along one direction while applying a large static electric field perpendicular to the film surface. There-after, when the film is strained along the stretched axis, a charge separation occurs with one surface of the film becoming negative and the opposite surface becoming positively charged. The charge density is proportional to the strain, which is in turn proportional to the applied stress. In sensor and actuator applications, the opposing surfaces of the film are metalized and connected to electrical leads.

Figure 28:
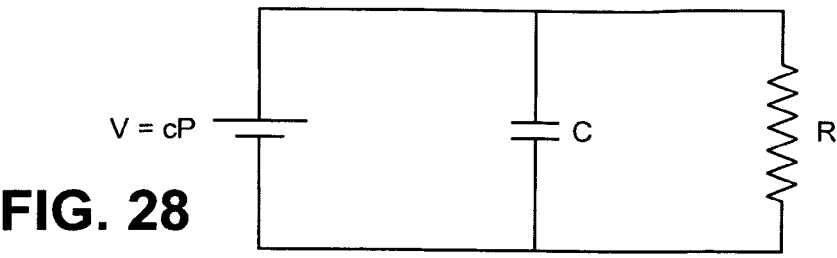
FIG. 28 is a drawing of an equivalent electrical circuit for a piezoelectric film, according to an exemplary embodiment of the present invention.

A piezoelectric film sensor has a built in high-pass filter property, as illustrated in the film equivalent circuit shown in FIG. 28. When a static pressure (stress) is applied to the film, a charge separation occurs and a voltage V can be measured between surface electrodes that is proportional to the applied stress. This voltage source is illustrated on the left-hand side of the equivalent circuit. The static charge that is stored as a result of the charge separation is modeled by the capacitor C of the equivalent circuit. Because the film has a large but finite electrical resistance, and because the measurement circuit also has a resistance that is not infinite, the charge will eventually bleed off the film surfaces and the voltage will decay to zero. Without an external load circuit, piezoelectric films have a decay time constant of thousands of seconds. Connecting an optional resistor across the film allows the time constant to be reduced by design, if one so desires. The parallel combination of the film resistance and any applied load resistance is modeled by the resistor R shown in the equivalent circuit of FIG. 28.

Piezoelectric films are also pyroelectric, generating a surface charge in response to a change in temperature. The pyroelectric voltage is proportional to the film thickness, and can be on the order of volts per degree Celsius for typical films having a thickness around 100 microns. Since temperature changes occur slowly in many environments (e.g. physiologic environments), the high pass filtering property of the films may reduce or eliminate thermal drift artifacts. Alternatively, an external load resistance can be established for this purpose.

One beneficial piezoelectric film for use in conjunction with the present invention is polyvinylidene fluoride (PVDF), which is also known as Kynar®. This film and copolymers of this film have been extensively developed as sensors. This piezoelectric film is a flexible, lightweight, tough engineering plastic available in a wide variety of thicknesses and large areas. As a transducer, the properties of piezoelectric film include:

Wide frequency range (0.001 Hertz to 1 Gigahertz).
Vast dynamic range ($10^{-8}$ to $10^6$ psi or μ-torr to Mbar)
Low acoustic impedance—close match to water, human tissue and adhesive systems
High elastic compliance
High voltage output—ten times higher than piezo ceramics for the same force input
High dielectric strength—withstanding strong fields (75 Volts/micron) where most piezo ceramics depolarize
High mechanical strength and impact resistance ($10^9$ to $10^{10}$ Pascal modulus)
High stability—resisting moisture (<0.02% moisture absorption), most chemicals, oxidants and intense ultraviolet and nuclear radiation
Can be fabricated into unusual designs
Can be glued with commercial adhesives
Biocompatible fluoropolymer PVDF can be applied as a thin film to the tissue-contacting surfaces of an implant. A small diameter vascular graft will be used as a specific example, however, many other implant possibilities exist, including those discussed elsewhere herein. Phasic changes in surface charge on a PVDF copolymer film are on the order of estimates for phasic changes in the membrane surface charge of the SMC layer underlying ECs in a native artery. The film material is very inert and biocompatible. Unlike sensor applications, in this application, no surface metallization is required because the film voltage is not being measured. The surface charge on the film itself is the desired property.

In an exemplary embodiment of a vascular graft, as noted above, the film 12 may be patterned, for example as either a spiral (FIG. 2) or a series of rings (FIG. 1) when placed on the cylindrical inner surface of the graft. The patterning improves the flexibility of the graft and also resembles the spiral pattern of SMCs in human arterial media. The similarity to arterial SMCs is further emphasized in the segmented option shown in FIG. 3. In this design, the spiral pattern of the film 12 is broken into segments ranging from a few to several hundred microns in length (e.g., from about 100 to 500 microns) and a few microns in width (e.g., from about two to ten microns) to mimic the dimensions of SMCs.

It is desirable, in some embodiments, to embed the film into the graft substrate material so that the blood-contacting surface is smooth, and the edges of the film are adjacent to graft material. The surface of the film inside the graft can be in contact with blood in some embodiments, with the opposing surface be electrically insulated from blood to avoid discharge of the opposing film surfaces. Alternatively, in some embodiments, the blood-contacting surface inside the graft can be coated, for example, with a thin electrically insulating, polar coating, such as a hydrophilic coating or other coating with a dielectric constant preferably ranging between that of the film (which is about 7.5 for PVDF copolymer film) and that of water (which is about 80).

In some embodiments, the material insulating the opposing film surfaces from one another (e.g. the graft material, as well as any surface coating, etc.) will be selected to have a high, but finite, electrical resistivity that bleeds charge from the film at a preferred rate (e.g., that associated with a high-pass filter time constant in the range of 10 to 100 seconds). This will eliminate surface charge accumulation due to body temperature changes while passing phasic charge variations at about 1 Hertz and above. Alternatively, the film itself has a resistivity which leads to charge decay, as discussed below.

Where a graft or other cylindrical device is formed, the film may be stretched in the circumferential direction and polarized in the radial direction. This process may be performed, for example, by passing a conductive rod through the graft, and placing the graft and rod within a conductive cylinder. The graft may be pressurized to induce wall stress and strain using, for example, fluid pressure and suitable feed-throughs for the rod. Once pressurized, a high voltage is applied between the conductive rod and the conductive cylinder to polarize the film. The polarity of the applied voltage determines the sign of the charge that will develop on the inside surface of the graft when it is re-pressurized.

Once polarized, pressure changes within the graft will cause wall stress in the piezo-active stretched direction. While there is a piezoelectric effect due to stress applied perpendicular to the film surface, this effect is about 1000 times smaller than for stress applied in the circumferential direction, and can be neglected. Thus, as pressure rises in the graft during systole, wall stress on the film causes a voltage to develop across the film thickness due to charge separation, with negative charge accumulating on the blood-contacting surface of the vascular graft. Where the charge returns to zero at diastole, it is proportional to the change in pressure above diastole blood pressure (the nominal DC level of pressure).

Table 1 depicts a table of typical properties of the PVDF piezoelectric copolymer film used in certain exemplary embodiments of the invention. These properties are used herein to compute electrical parameters in a typical vascular graft.

TABLE 1

Typical properties of piezo film

| Symbol | Parameter | PVDF | Copolymer | Units |
|---|---|---|---|---|
| t | Thickness | 9, 28, 52, 110 | <1 to 1200 | μm (micron, $10^{-6}$) |
| $d_{31}$ | Piezo Strain Constant | 23 | 11 | $10^{-12} \frac{m/m}{V/m}$ or $\frac{C/m^2}{N/m^2}$ |
| $d_{33}$ | | −33 | −38 | |
| $g_{31}$ | Piezo Stress constant | 216 | 162 | $10^{-3} \frac{V/m}{N/m^2}$ or $\frac{m/m}{C/m^2}$ |
| $g_{33}$ | | −330 | −542 | |
| $k_{31}$ | Electromechanical | 12% | 20% | |
| $k_t$ | Coupling Factor | 14% | 25-29% | |
| C | Capacitance | 380 for 28 μm | 68 for 100 μm | pF/cm² @ 1 KHz |
| Y | Young's Modulus | 2-4 | 3-5 | $10^9$ N/m² |
| $V_0$ | Speed of    stretch: | 1.5 | 2.3 | $10^3$ m/s |
|  | Sound    thickness: | 2.2 | 2.4 | |
| p | Pyroelectric Coefficient | 30 | 40 | $10^{-6}$ C/m² °K |
| e | Permittivity | 106-113 | 65-75 | $10^{-12}$ F/m |
| $e/e_0$ | Relative Permittivity | 12-13 | 7-8 | |
| $\rho_m$ | Mass Density | 1.78 | 1.82 | $10^3$ kg/m |
| $\rho_e$ | Volume Resistivity | >$10^{13}$ | >$10^{14}$ | Ohm meters |
| $R_\square$ | Surface Metallization | <3.0 | <3.0 | Ohms/square for NiAl |
| $R_\square$ | Resistivity | 0.1 | 0.1 | Ohms/square for Ag Ink |
| tan $\delta_e$ | Loss Tangent | 0.02 | 0.015 | @ 1 KHz |
| | Yield Strength | 45-55 | 20-30 | $10^6$ N/m² (stretch axis) |
| | Temperature Range | −40 to 80 . . . 100 | −40 to 115 . . . 145 | °C. |
| | Water Absorption | <0.02 | <0.02 | % $H_2O$ |
| | Maximum Operating Voltage | 750 (30) | 750 (30) | V/mil(V/μm), DC, @ 25° C. |
| | Breakdown Voltage | 2000 (80) | 2000 (80) | V/mil(V/μm), DC, @ 25° C. |

First, the voltage developed across the film in response to blood pressure is computed. Blood pressure creates a circumferential wall stress in the plane of the film given by Laplace's law:

$$S_{wall} = P(D/2t) \quad (1)$$

where $S_{wall}$=wall stress in N/m²
D=graft inside diameter in meters
t=film thickness in meters
P=blood pressure in N/m²

It is assumed that the wall stress is concentrated in the piezoelectric film rather than in the graft substrate material. This is likely to be true for the patterns of FIGS. 1 and 2 because the Young's modulus of the film is similar to that of polycarbonate (approx. 2.4 GPa), and is much larger than the modulus of typical graft materials, such as Teflon (approx. 0.5 GPa). For the patterns of FIG. 3, unpolarized PVDF may be used for the substrate to provide a uniform modulus, if desired.

The voltage developed across the film in response to the circumferential wall stress is given by:

$$V = G_{31} S_{wall} t \quad (2)$$

where

V=film voltage in volts
$G_{31}$=piezo stress constant in Volt-m/N
Combining equations (1) and (2) gives:

$$V = G_{31} PD/2 \quad (3)$$

Note that the voltage developed is independent of the film thickness. Since the film does not respond to DC or ambient blood pressure, Equation (3) can be written as:

$$\delta V = G_{31} \delta PD/2 \quad (4)$$

where δP is the difference between systolic and diastolic pressures, typically about 40 mmHg or 5,000 N/m². Consider a 4 mm diameter graft and a typical piezoelectric copolymer film having $G_{31}$=0.16 V-m/N. Equation (4) yields:

$$\delta V = 1.6 \text{ Volts for a 4 mm i.d. vascular graft} \quad (5)$$

While this voltage is much larger than the change in SMC membrane potential with pressure, estimated at 0.02 Volts, the SMC membrane is very thin, so the surface charge density needed to create the membrane potential is correspondingly large. The surface charge on the piezoelectric film blood-contacting surface can be computed and compared to the SMC surface charge. First, the film capacitance is determined by:

$$C = \epsilon_0 \epsilon A/t \quad (6)$$

where $\epsilon_0$=8.85 H $10^{-12}$ Farad/m
$\epsilon$=7.5 (typical value for piezoelectric copolymer film)
A=film area in m²
C=film capacitance in Farads The surface charge density change during systole is then given by:

$$\delta\sigma = \delta q/A = C\delta V/A \quad (7)$$

or $$\delta\sigma = \epsilon_0 \epsilon \delta V/t \quad (8)$$

Equation (8) shows the inverse proportionality between surface charge density and film thickness. The same formula applies to the SMC membrane, in which t is the membrane thickness, which is only about 10 nm. To increase the surface charge density, the thickness of the piezoelectric film is decreased. However, a lower limit on film thickness is the value for which wall stress exceeds the yield stress of the film. From equation (1) we write an upper limit on the wall stress as:

$$S_{wall} = (D/2t)P_{max} < S_{yield} \quad (9)$$

The upper limit on patient blood pressure will be taken here as 240 mmHg or 3 H $10^4$ N/m². The yield stress of a typical copolymer piezoelectric film is 2.5 H $10^7$ N/m². Thus, equation (9) yields for the 4 mm artery under consideration:

$$t > 2.4 \times 10^{-6} m = 2.4 \text{ microns}$$

As an engineering factor, if we specify t=5 microns for the film thickness, Equation (8) then yields a surface charge density of 20 µC/m². To compare this with the SMC membrane surface charge, consider Equation (8), which applies to both charge separation in a piezoelectric film and to charge separation across a cell membrane. Since the membrane dielectric constant is unknown, we take it to be approximately equal to the film dielectric constant for the purpose of estimation and find:

$$(\delta\sigma_{membrane}/\delta\sigma_{film}) = (\delta V_{membrane}/\delta V_{film})(t_{film}/t_{membrane}) = (0.02/1.6)(5/0.01) \approx 6. \quad (10)$$

Since the surface charge densities are in the same order of magnitude, a 5-micron piezoelectric film should suffice. Alternatively, a thinner piezoelectric film can be adhered to a substrate with higher yield stress or greater thickness. Piezoelectric films as thin as 20 nm are possible, although piezoelectric films in the range of 0.5-1.0 micron are expected to be sufficient, and film thicknesses covering the range of 0.1 to 10 microns should cover a useful-range of for stimulating films attached to implant surfaces. Some implants, for example stents, may be constructed entirely from PVDF, with thickness in the range of 50 to 200 microns. The PVDF may be fully polarized, or constructed from multiple layers, with only the blood-contacting layer of PVDF being polarized Next, consider the pyroelectric effect in these films. The pyroelectric voltage developed across the film is given by:

$$V_p = pA/C = pt/\epsilon_0\epsilon \quad (11)$$

where
$V_p$=pyroelectric voltage in volts per degree C.
p=pyroelectric coefficient=$4 \times 10^{-5}$ for copolymer film Thinner films have the advantage of a reduced temperature coefficient. For the five micron film considered above, Equation (11) yields $V_p$=0.03 volts/degree C. Considering the 1.6 volt phasic change in film potential, this relatively small change with temperature should be negligible, especially at the one Hertz time scale of a normal heart rate.

Finally, consider the decay time constant of film, which is given by:

$$\tau = RC = (\rho t/A)(\epsilon_0\epsilon A/t) = \epsilon_0\epsilon\rho \quad (12)$$

where
R=film resistance in Ohms
$\rho$=film resistivity in Ohm-m

An estimate of film resistivity is $10^{14}$ Ohms-m. While this resistivity is very large, it is still finite and Equation (12) yields $\tau$=6600 seconds or 1.8 hours. It may be desirable in some embodiments to reduce this time constant by adding a resistance in parallel with the film. This might be provided, for example, by supplying a poorly conducting coating along the edges of the film, or by proper selection of the substrate polymer material of the graft, if any.

Finally, the electrical properties of the film are analyzed in the context of wound healing. During systole, a lateral electric field is set up with its negative pole at the graft or patch center. The magnitude of this field can be estimated near the margins of the implant. For example, the electric field near the opening of the polarized vascular graft can be computed numerically in terms of two oppositely charged, cylindrical surfaces with surface charge density computed from Eq. (8) as 20 µC/m². The result is on the order of 1 Volt/cm near the graft ends and directed into the graft, decreasing to zero at the graft mid point. This field is on the order of magnitude of fields observed near the margins of wounds. Application of external electric fields of this magnitude has been shown to speed wound healing. Such fields also have been shown to cause EC migration towards the negative pole, and to stimulate mitosis. These observations offer separate support for selecting the negative polarity of the graft. As discussed elsewhere, the correct magnitude of the phasic surface charge density may be chosen to be equal to the surface charge density of neighboring vascular endothelium. This is also similar to the surface charge density of the substrate of smooth muscle underlying the endothelium. An estimation of the phasic variations in EC and SMC surface charge is provided below.

Membrane Potential

The following sections derive a formula for the electrostatic membrane potential and its relationship to blood pressure.

Figure 5:
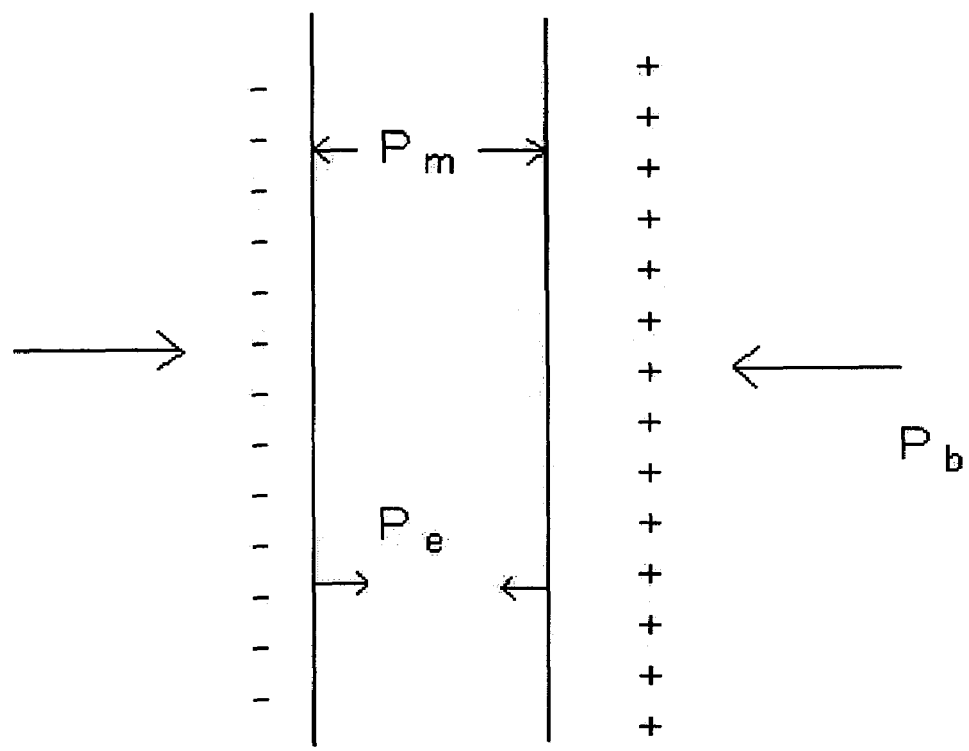
FIG. 5 depicts a schematic representation of a cell membrane modeled as a capacitor, and indicates the balance of electrostatic and blood pressures.

All cells have a lipid membrane surface. The cell membrane has the unique property of electrical charge separation across the membrane, with the inside surface of the cell negatively charged and the outside surface positively charged. In an ionic fluid environment, the positive outside surface of the cell attracts large, negative ionic species that become fixed to the cell surface forming the glycocalyx. Thus the net surface charge on blood contacting cells is negative, dominated by the glycocalyx 195, as illustrated in FIG. 19. The cell surface becomes more negative as the cell membrane 194 depolarizes and positive ions leave the region of the glycocalyx 195 to enter into the cell. Since the glycocalyx 195 charge is fixed and does not respond to pressure, the bare cell membrane is considered here. The electric field and the resulting electrostatic pressure acting on the membrane surfaces are computed. A small section of the cell membrane is sketched in FIG. 5, illustrating the charge separation, the electrostatic pressure of attraction between the oppositely charged surfaces, $P_e$, blood pressure, $P_b$, and internal membrane pressure, $P_m$.

The cell membrane may be modeled as a capacitor whose lateral dimensions are much larger than its thickness. The energy stored on the capacitor plates is given by:

$$U = (\tfrac{1}{2})CV^2 \quad (13)$$

where
V=membrane potential in Volts
C=membrane capacitance in Farad/m
U=Energy stored in the capacitor in Joules The formula for membrane capacitance is identical to the formula for the capacitance of a piezoelectric film, and is given by Eq. (6). The force of attraction between the membrane layers is given by:

$$\vec{F} = -\nabla U \quad (14)$$

where $\vec{F}$ =vector force between membrane surfaces in Newtons
$\nabla$=gradient operator=$\partial/\partial t$, where t is the membrane thickness
U=electrostatic energy within the membrane Combining Eqs. (6), (13), and (14) and dividing the force by the membrane surface area then yields:

$$P=(\epsilon_0 \epsilon/2)(V/t)^2 \quad (15)$$

where

P=electrostatic pressure within the cell membrane in Newtons/meters$^2$

The pressure given by Equation (15) draws the two membrane surfaces together. It is balanced by the difference between the pressure inside the membrane and the fluid pressure within the cell and in the extra-cellular space. The pressure within the membrane is a consequence of osmotic pressure and the electrostatic forces between the tails of the lipid molecules within the membrane. The pressure outside the cell is equal to local blood pressure, while the pressure within the cell is also equal to local blood pressure. This is true because the cell membrane is permeable to water (but not to ions). Blood pressure must be equilibrated within and without the cell to maintain a constant cell volume.

To evaluate Equation (15), we use a typical membrane thickness of 8 nanometers. Because a value for the membrane dielectric constant was not identified, a simple assumption is made that the dielectric constant is roughly the average of oil (presumably close to that of the lipids within the membrane), $\epsilon=3$, and water, $\epsilon=80$ which permeates the membrane, or $\epsilon=41.5$. Equation (15) is plotted in FIG. 6, as membrane electrostatic pressure in millimeters of Mercury (Hg) versus the membrane potential in milliVolts. The electrostatic pressure acts to collapse the membrane due to the attraction of positive and negative membrane surfaces. So with increasing negative membrane potential, the membrane pressure rises in a non-linear manner.

The electrostatic pressure in Equation (15) may be set equal to the difference in pressure within the membrane and blood pressure. Changes in SMC membrane potential may lead to constriction of the SMC, presumably due to the opening of voltage activated calcium channels in the membrane wall. Here it is shown that the reciprocal is also true, namely changes in blood pressure cause changes in SMC membrane potential, again due to the flow of ions across the membrane to reduce the potential when blood pressure increases. Changes in membrane potential with pressure also occur in the EC layer and the changes may in fact be initiated in the EC layer, and propagated to the SMC layer, or vice versa. The pressure effect is predicted from Equation (15) by solving for membrane potential in terms of blood pressure. First note that:

$$P_m-P_b=(\epsilon_0 \epsilon/2)(V/t)^2 \quad (16)$$

and $$P_m-P_d=(\epsilon_0 \epsilon/2)(V_0/t)^2 \quad (17)$$

where $P_m$=pressure within the membrane
$P_b$=blood pressure
$P_d$=diastolic blood pressure
$V_0$=resting membrane potential Equations (16 and 17) assume that the pressure within the cell does not change significantly with blood pressure. This is true because the membrane does not contain a significant ion concentration, so osmotic pressure is determined by the bulk ion concentrations inside and outside the cell. Electrostatic repulsion between the lipid tails may also be nearly constant. Equation (17) is written for the case of blood pressure equal to diastolic pressure, during which time the membrane potential is taken as the "resting" membrane potential (about −60 mV for SMCs). Subtracting Equation (16) from Equation (17) and rearranging terms gives:

$$V=V_0\sqrt{1-(P_b-P_d)/P_0} \quad (18)$$

where $$P_0=(\epsilon_0 \epsilon/2)(V_0/t)^2 \quad (19)$$

Figure 6:
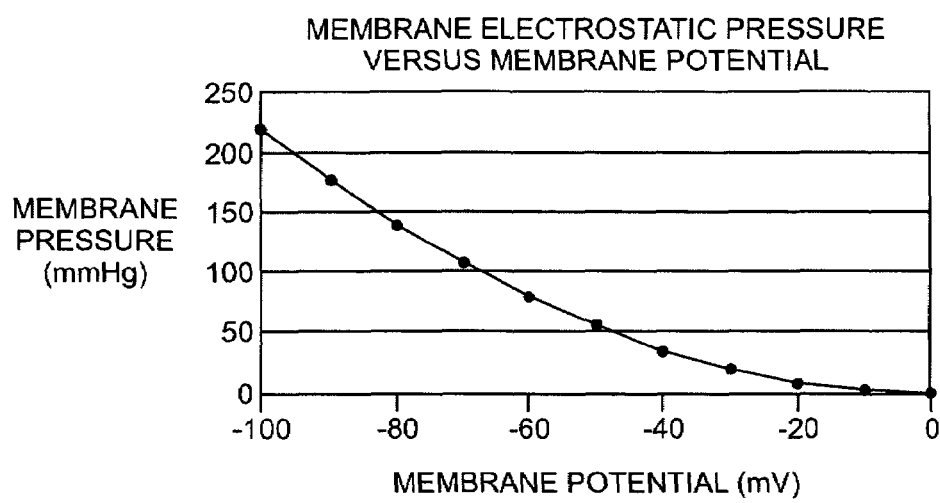
FIG. 6 depicts a plot of the membrane electrostatic pressure versus membrane potential.
Figure 7:
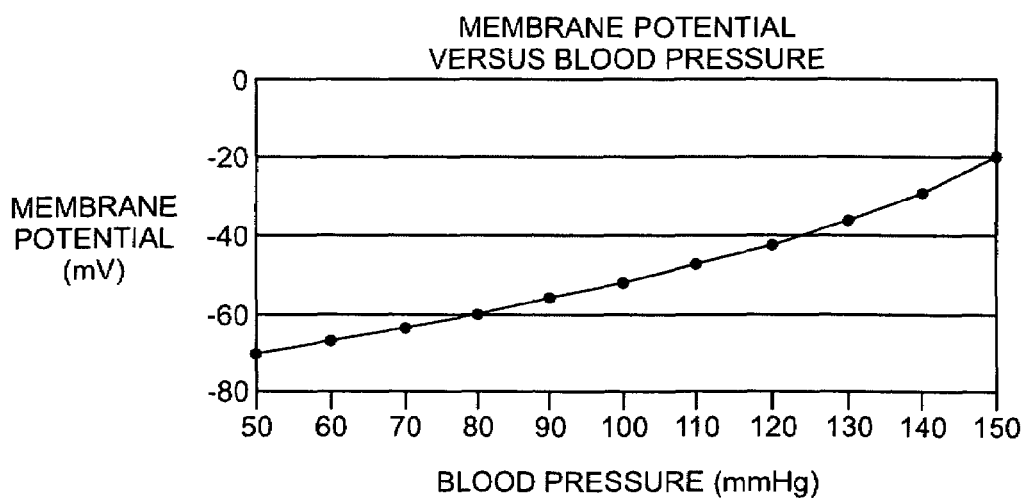
FIG. 7 depicts a plot of the membrane potential versus blood pressure.

If we take the resting membrane potential as −60 mV, then we see from Equation (15) or FIG. 6 that $P_0$=78.5 mmHg. Equation (18) is plotted in FIG. 7 as membrane potential versus blood pressure. The parameters assumed for the SMC include: resting potential=−60 mV at diastolic pressure of 80 mmHg; $\epsilon$=41.5 (an average of lipid and water values); membrane thickness=8 nm. If systolic pressure is taken as 120 mmHg, FIG. 7 predicts a change in resting potential of about 18 mV between diastole and systole. This is a reasonable change for SMCs and ECs.

Figure 15:
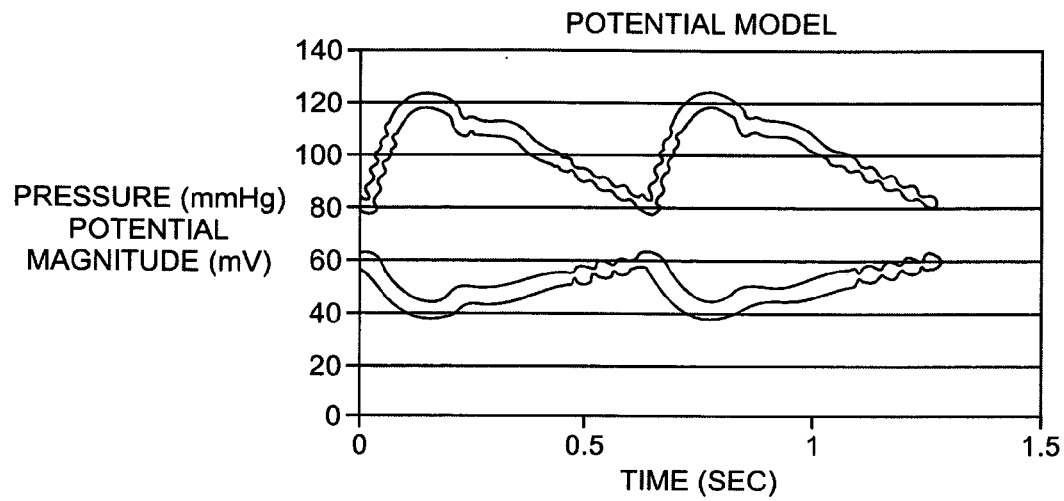
FIG. 15 depicts a plot of blood pressure data and membrane potential model versus time, showing phasic waveforms.

FIG. 15 shows a plot of blood pressure and membrane potential versus time, showing the phasic pressure and membrane potential waveforms. The pressure waveform was taken from a textbook, while the membrane potential was computed from blood pressure using Eq. (18).

The action potential of SMCs and ECs are coupled. Specifically, in coronary arteries the two cell types touch through fenestration or gaps in the internal elastic lamina. Simultaneous depolarization in the membrane potential of ECs and SMCs is found under the influence of applied arterial pressure.

Depolarization of the SMCs with increased blood pressure occurs with or without an endothelial covering. Relaxation or increase in SMC membrane potential occurs when the blood shear rate is increased at constant arterial pressure. This effect only occurs when EC cells cover the SMC layer.

According to current teaching, increased pressure reduces the membrane potential, which then opens voltage activated calcium channels in the membrane, causing the SMCs to constrict. Here we suggest a more detailed understanding of this phenomena: positive ions pass through the membrane when pressure is increased, reducing the membrane potential and the electrostatic membrane pressure, to maintain homeostasis of total pressure on the membrane. The membrane potential is not reduced enough to open calcium ion channels and trigger an action potential by normal diastolic to systolic blood pressure variations. When blood pressure rises above a critical value, however, the membrane potential is reduced enough to open calcium ion channels, resulting in constriction of the SMCs and narrowing of the blood vessel lumen.

For the purposes of this invention, the theory of membrane potential variation does not need to be invoked. The fact that phasic variations in the charge density do occur on blood contacting surfaces is assumed, and the invention provides means to stimulate implant surfaces to mimic the native substrate, for example, to encourage endothelium to cover and heal the implant, to stimulate implant surfaces in a manner that is contrary to the native substrate, for example, to discourage tissue growth, and so forth. For example, in some embodiments, stimulation is provided in phase with blood pressure, and in an embodiment that is particularly elegant in its simplicity, a piezoelectric film automatically provides a phasic charge density on the surface that mimics the native substrate.

It is known that a variety of local chemical signals and nerve impulses can alter the membrane potential of SMCs and ECs. Chemical signals may pass between the EC and SMC, or they may communicate via electrostatic interactions. Depolarization signals propagate much more rapidly through the tight junctions of the EC layer than they do through the SMC layer. Signals for SMC constriction/relaxation originate in, or propagate through, the EC layer, and then down through EC-SMC gap junctions to the SMC layer. This is true for both chemical and blood pressure induced signaling. The myoendothelial contacts might also be regarded as sites where biomechanical forces (shear stress, blood pressure) are transduced directly from ECs to SMCs.

Additional Methods and Devices for Influencing Cell Growth

Whether phasic changes in membrane potential are caused by mechanical, chemical, or electrical (depolarization wave) signals, various embodiments of the present invention provide various techniques for detecting the phasic signals and transduce them into appropriate surface charge phasic variations on an implant surface.

Figure 8:
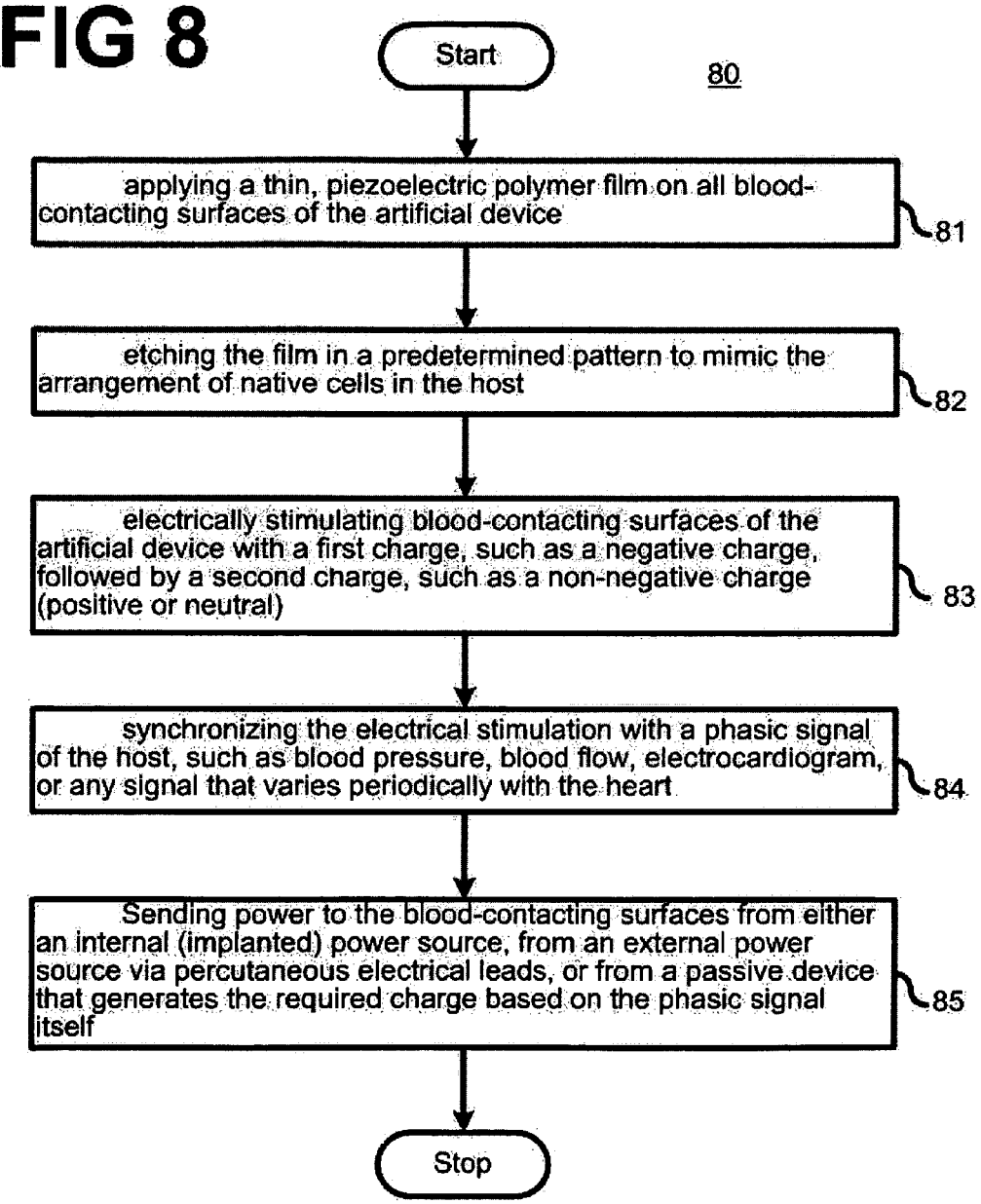
FIG. 8 depicts an exemplary embodiment of a method for forming and operating an artificial device in a host according to one aspect of the present invention.

Turning now to FIG. 8, shown therein is an exemplary embodiment of a method for forming and operating an artificial device according to an aspect of the present invention. In this embodiment, in element 81, a thin, piezoelectric polymer film is applied on all tissue-contacting surfaces of device. This step may be performed during a process for manufacturing the device. Alternatively, flexible electrodes are placed under the tissue-contacting (e.g., the inside and outside) surfaces of the implant.

In element 82, the film can be etched in a predetermined pattern, for example, to mimic the arrangement of native cells in the host. The etching pattern can be selected, for example, from those shown in FIGS. 1-3, or can be any solid or patterned film that simulates the electric field created by the native tissue. As with element 81, this step may be performed during a manufacturing process of the device.

In element 83, all tissue-contacting surfaces of the device are electrically stimulated with a first charge, such as a negative charge, followed by a second charge, such as a less-negative or non-negative charge (e.g., a positive or neutral charge). This step may be performed, for example, once the device is implanted in the host to promote EC growth on the blood-contacting surfaces of the device. (Alternatively, this step may also be performed ex vivo, for example, to promote endothelial growth, or "seeding," prior to implantation.) As discussed above, in some embodiments, the stimulation waveform may be altered, reduced in magnitude, or discontinued as the surface heals.

In element 84, the electrical stimulation described in element 83 is synchronized with a phasic signal of the host, such as blood pressure, blood flow, electrocardiogram, tissue stretch, or any other signal that varies periodically (e.g., with the heart). This allows the surface charge of the implant to mimic the surface charge that develops, for example, in the vicinity of the ECs. In this step, the phasic signal may include a first portion and a second portion, in which the first charge is synchronized with the first portion of the phasic signal and the second charge is synchronized with the second portion of the phasic signal. For example, when blood pressure is used as the phasic signal, the diastolic phase of the blood pressure can be the first portion of the phasic signal and the systolic phase of the blood pressure can be the second portion of the phasic signal. Moreover, the specific phases may be selected based on the location of the implant. For example, as mentioned above, the optimum stimulation sequence may be different for different tissue. For example, if the implant is located in a peripheral artery, which is perfused during systole, the surface charge will be negative during the systolic phase of blood pressure as pressure is increased in this phase, whereas if the implant is located in a coronary artery, which is perfused during diastole (because the heart squeezes the distal arteries during systole), the surface charge can be made negative during the diastolic phase of blood pressure, if desired. Thus, the optimum stimulation sequence may be different for various blood vessels, including coronary and peripheral arteries. The stimulation waveform may be a non-linear function of the phasic signal, for instance, in both amplitude and phase. As one example, the stimulation waveform may be a square wave while the phasic input is a sine wave. The stimulation waveform may be shifted in phase by up to +/−180° from the input signal.

In element 85, it is indicated that the electrical stimulation of elements 83 and 84 is achieved by generating charge at the tissue-contacting surfaces using, for example, an internal (implanted) power source, an external power source (via, for example, percutaneous electrical leads or inductive or capacitive power coupling), or a passive (e.g., piezoelectric) device that generates the required charge from the phasic signal itself. Thus, the piezoelectric film of element 81 may produce the charge directly in response to phasic pressure variations, or the film may be used to generate and store charge that is routed to embedded electrodes in response to a phasic input.

Figure 9:
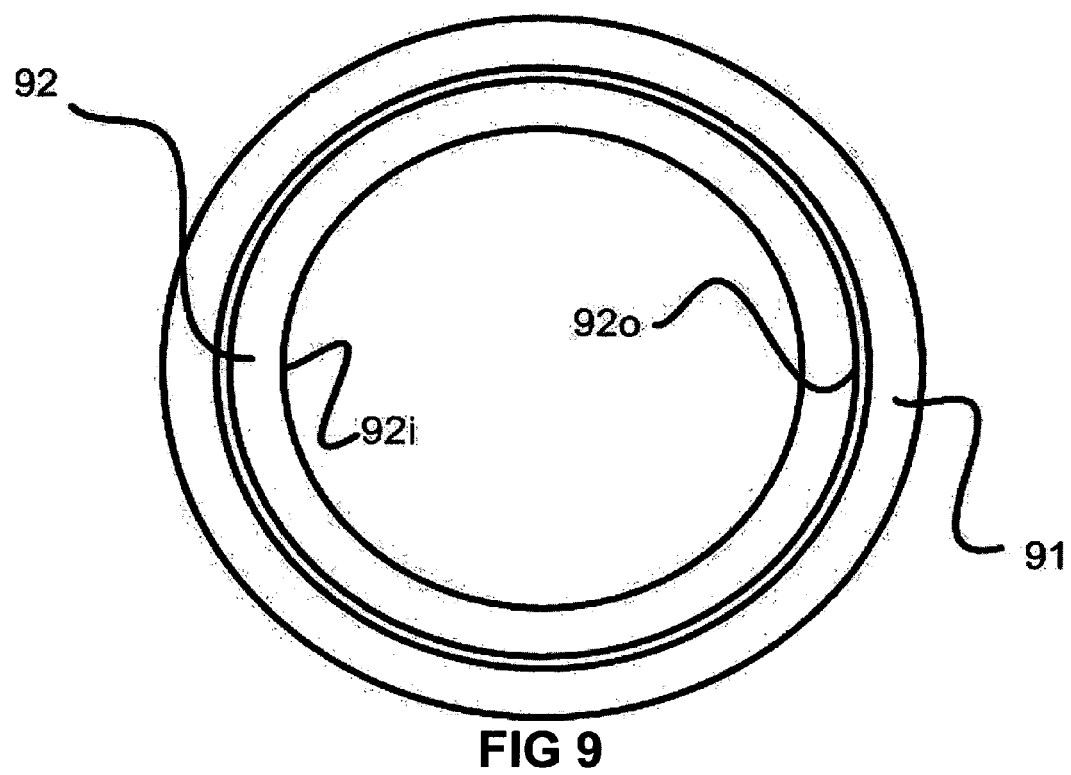
FIGS. 9-13 depicts various exemplary embodiments of implant devices, according to various exemplary embodiments of the present invention.

Turning to FIG. 9, shown therein is an exemplary embodiment 90 of an implant according to an aspect of the present invention. FIG. 9 depicts a cross section of a portion of the exemplary embodiment of the device 90, which in this case is of tubular construction. The external member 91 is not in contact with blood. Thus, the material selected for this member 91 can be selected based on other criteria, such as strength-to-weight ratio, to name only one example. Examples of suitable materials for external member 91 include polymers such as polyesters (e.g., DACRON) and expanded polytetrafluoroethylene (ePTFE). The inner member 92 in this embodiment is constructed of an electromechanical transducing material such as polarized PVDF. In this regard, the external member 91 may be constructed from non-polarized PVDF. While a space is shown between the inner member 92 and the outer member 91, this is for illustration purposes only.

As blood pressure increases in the central lumen of the device, a charge separation develops between the inner surface of the film 92$i$, which is in contact with the blood and the outer surface of the film 92$o$, which is in contact with the external member 91 of the device 90. Thus, a negative charge develops on the blood contacting inner film surface 92$i$. As the blood pressure decreases, a less negative or neutral charge develops on the inner film surface 92$i$. The film 92 is polarized (i.e., oriented) in this embodiment so the blood-contacting surface becomes negatively charged in response to increasing blood pressure. In addition, a fixed negative (or positive) charge may be present on surface 92$i$ due to hydration of negative charge groups on that surface, providing a charge offset, if desired. Moreover, the film 92 in this exemplary embodiment includes an internal resistance selected to provide a high-pass filter time constant of between approximately two seconds and approximately one hundred seconds. One possible embodiment of the film 92 includes a polyvinylidene fluoride copolymer. The thickness of the film 92 can be between approximately 0.1 microns and approximately 10 microns, with the exact thickness being readily determined through simple experimentation.

The device 90 can be, for instance, a synthetic prosthesis, a vascular graft, a blood pump chamber, a heart valve, a venous valve, an in-dwelling catheter, an implanted filter, or a stent, to name only a few examples. In general, the device 90 can represent any artificial device or implant that comes in contact with blood or blood-like fluids, in which cell growth on a surface in contact with the blood-like fluid is desired.

In some applications it may be desirable to polarize the film, 92, so that the inside surface becomes positively charged in response to increasing blood pressure. In some physiologic settings, for example, coronary arteries, this reversed polarity may promote healing. In other applications, the reverse polarity may be used to inhibit cell proliferation, for example to prevent restenosis or to inhibit blood vessel growth into tumors.

As noted above, it may be desirable in some embodiments to coat surface 92i. For example, surface 92i may be provided with a material, such as those discussed above, that becomes either positively or negatively charged upon hydration by blood. By varying fixed surface charge and film polarity, a wide variety of phasic waveforms can be produced. Further variations in phasic waveform may be produced by selection of a coating on surface 92i having an electrical resistivity that produces a given electrical filter characteristic. The coating on surface 92i may be selected, for example, to have a dielectric constant that falls between the dielectric constant of the piezoelectric film and that of blood.

Figure 10:
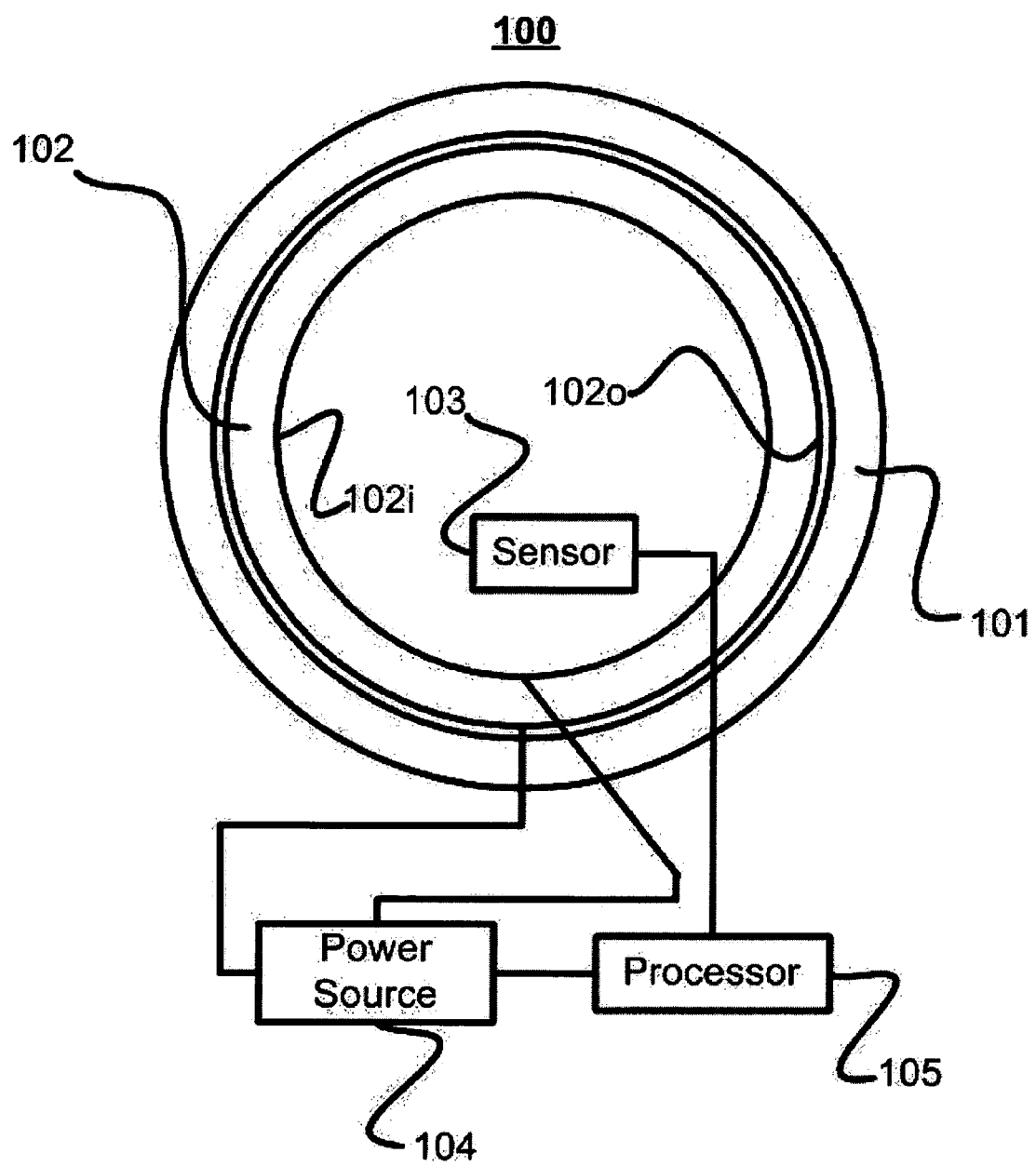

Turning to FIG. 10, shown therein is an alternative embodiment of a device 100 for implanting in a host, such as a human body. In this case, an active power source 104 is used to apply a voltage across the inner member 102 (e.g., a film or other material) that is provided at the inner surface of an outer member 101 of the device 100. A sensor 103 monitors a desired phasic signal, such as blood pressure, pulse, electrocardiogram or other periodic signal. The location of the sensor 103 will vary depending upon the desired phasic signal. In the case of blood pressure, the sensor could be disposed in the bloodstream essentially anywhere in the host. A processor 105 can be programmed to apply the proper charge to inner surface 102i of the film 102, at the suitable times in synchronization with the phasic signal. For example, a thin piezo electric film could be used as a sensor 103 to monitor the blood pressure, and the charge developed therein could be used to indicate to the processor the difference between diastole and systole. The processor 105 could then be programmed to apply an appropriate voltage across the film 102 to create any desired surface charge density in synchronization with the phasic signal. Moreover, the processor 105 and/or power supply 104 can be disposed internally or externally to the host, depending on the application. Furthermore, the processor can be programmed to operate for only certain lengths of time until healing is expected to be complete, or perpetually, depending upon the application.

Figure 11:
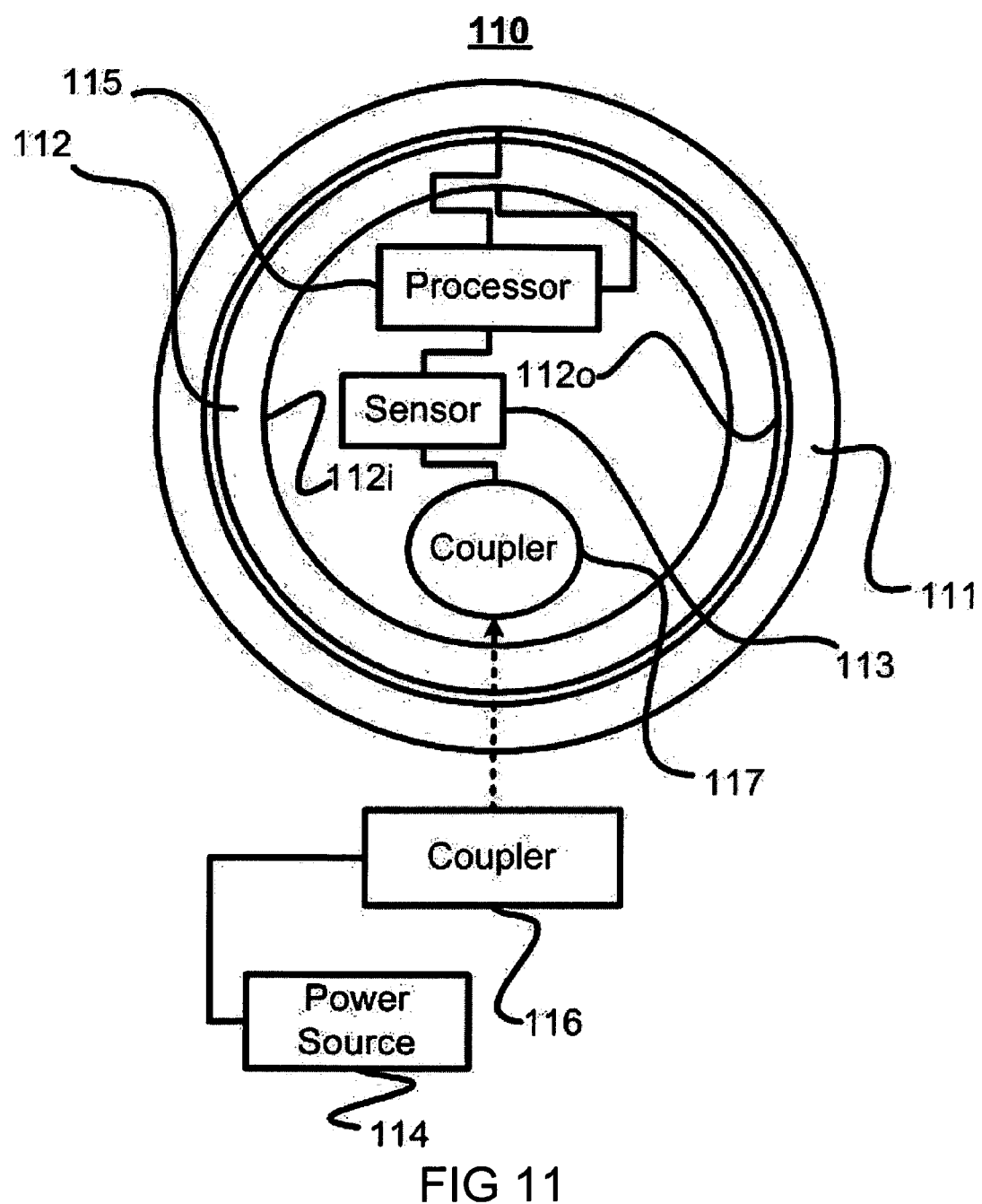

Turning to FIG. 11, shown therein is another exemplary embodiment 110 of a device in accordance with the present invention. In this embodiment 110, power from the power source 114 is coupled to an embedded processor 115 and sensor 113 via couplers 116, 117. These couplers can operate, for example, via magnetic field induction or capacitive coupling. Thus, power is fed to the processor 115 and sensor 113 via this coupling through the skin of the host. The processor 115 in turn activates the charge in the desired manner on the inner surface 112i of the film 112.

Figure 12:
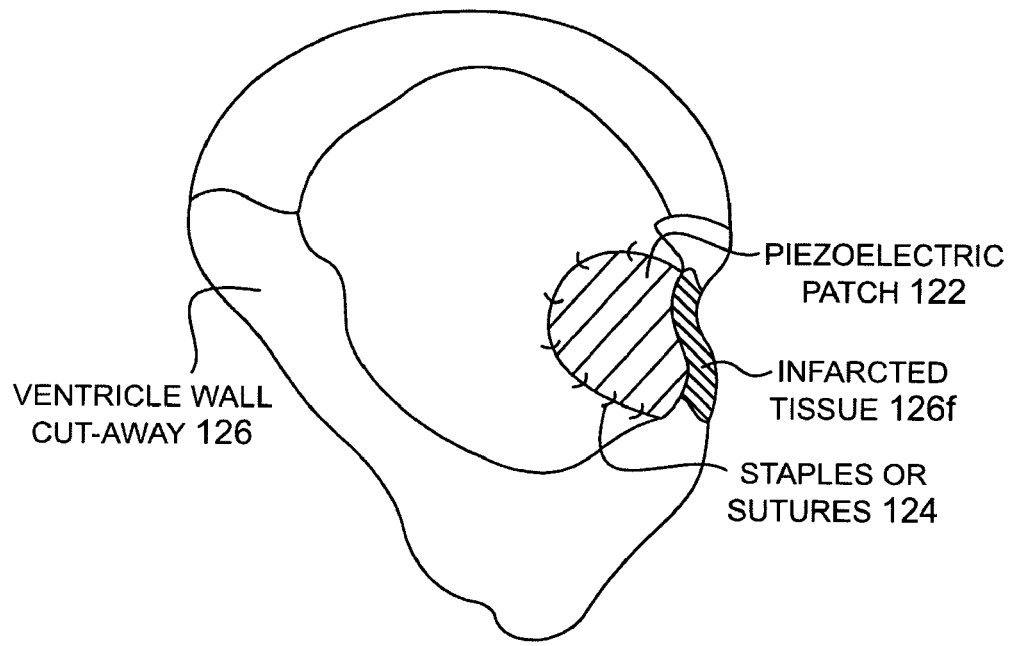

Turning now to FIG. 12, shown therein is another embodiment of the present invention, comprising a piezoelectric film patch 122 attached to the inside surface of a ventricle 126 of the heart over a region of myocardial infarction 126f. As described above, and especially with reference to FIGS. 4b, 18a and 18b, the tissue surrounding the infarction is polarized, and phasically depolarizes on each contraction of the heart. The tissue comprising the infarction scar 126f, however, is not significantly polarized, and does not significantly charge polarity. A current of injury therefore flows from the normal tissue into the scar region 126f on each heartbeat. A piezoelectric film patch 122 is therefore attached to the normal tissue at the margins of the infarct, and covers the infarct scar 126f, either on the inside of the ventricle as shown in FIG. 12, or on the epicardial surface, or both. Attachment is envisioned using staples or sutures 124, and may be performed surgically or percutaneously under image guidance. The patch 122 may be strained during placement, so that when the heart contracts during systole the strain is released, and the patch 122 depolarizes in synchrony with surrounding tissues. By this means, the current of injury flowing into the infarct zone 126f from the normal cells at the infarct margins is reduced or eliminated. ECs can then migrate to cover the patch 122. It is believed that myocardial cells, perhaps originating as stem cells from the blood, may then fill in under the endothelial layer. The patch 122 may also be coated on its inside surface or impregnated with suitable growth factors that encourage in-growth of myocardium. As shown in FIG. 18, patches may be placed on the endocardial and/or epicardial surfaces of the heart. It is also noted that an active patch, analogous to the electric bandage of FIG. 17b, may be used to provide a phasic current of injury to the tissue. The central bandage electrode would contact tissue in the infarct zone, and the second electrode would contact normal tissue outside the infarct zone. A sensor detecting a phasic parameter such as the local ECG signal or blood pressure would then drive current into or out of the infarct zone in phase with the depolarization and re-polarization of surrounding tissue. Alternatively, discrete electrodes could be attached to the surface of the heart or be implanted in the heart wall to provide the phasic injury current in the infarct zone from a suitable source of electrical energy.

Figure 13:
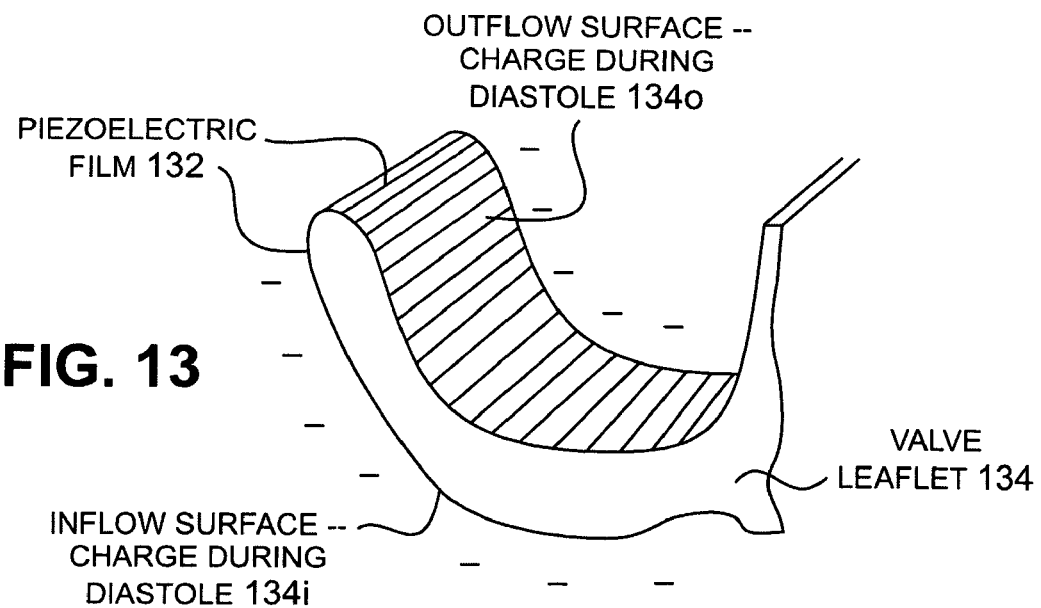

FIG. 13 shows yet another embodiment of the present invention. A synthetic heart valve is shown. In the embodiment shown, it is constructed from a flexible polymer, which may be internally reinforced with fibers, although other constructions are clearly possible. The outside surface of the valve leaflet 134 is coated with a thin piezoelectric film 132, polarized such that the outside surface charge is negative during diastole. The valve leaflet 132 is shown during diastole, when the inflow side is relaxed and the outflow side is stretched. In this embodiment, the inflow surface 134i and the outflow surface 134o of the valve leaflet 134 are both negative during diastole, and neutral or positive during systole. This selection is made to electrically repel negatively charged blood components such as platelets and proteins, which may otherwise settle on the surfaces when the blood is more quiescent during diastole. The negative charge is also provided to encourage ECs to cover the leaflets. During systole the inflow and outflow surfaces 134i, 134o will become neutral or positively charged. Note that the piezoelectric film 132 on the outflow surface 134o is stretched during diastole, and it thus may be polarized with its blood-contacting surface becoming negative under stretch. The inflow surface 132i, on the other hand, is relaxed during diastole, and may require treatment with fixed charge groups, for example, groups that become negative when the film is hydrated by blood. In this embodiment, the film 132 on the inflow surface 132i may be polarized with the blood contacting surface becoming positive during systole when it is stretched. When the inflow surface 132i of the valve 134 is stretched during systole, the fixed negative charge is countered by the piezoelectric positive charge. On the other hand, where the film 132 on the inflow surface 132i is polarized with the blood contacting surface becoming negative when stretched, it will be negative both during systole, when it is stretched, and during diastole, when it is relaxed (due to the presence of the fixed negative charge).

Other embodiments of the invention include various choices of plus, minus or neutral charge during systole and diastole for the two surfaces. More complex stimulation may be achieved through embedded electrodes energized in response to sensor signals. Simpler stimulation may be achieved by constructing the valve from an electromechanical transducing material such as PVDF, and polarizing in either the systolic or diastolic configuration. In still other embodiments, the valve is constructed using a electromechanical transducing material such as PVDF, which is polarized in either the systolic or diastolic configuration, and is also provided with embedded electrodes that are energized in response to sensor signals.

Figure 29A:
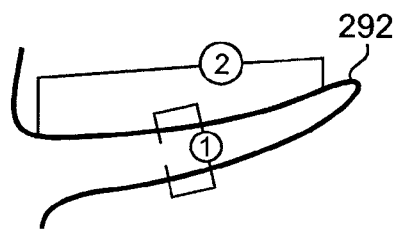
FIGS. 29a through 29f are schematic drawings that illustrate strategies for stimulation of a heart valve, in accordance with various exemplary embodiments of the present invention.
Figure 29D:
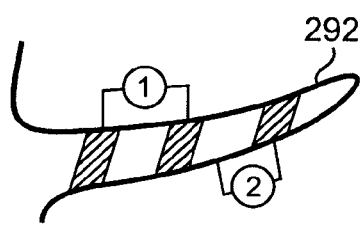
Figure 29B:
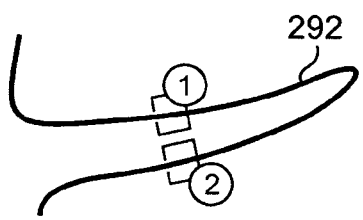
Figure 29E:
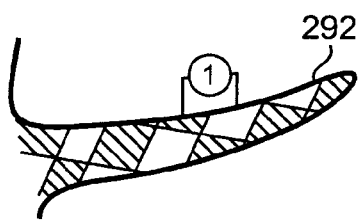
Figure 29C:
Figure 29F:

FIGS. 29A-29F schematically illustrate several heart valves 292 incorporating various aspects of the present invention. For example, portions of the heart valve 292 can incorporate electrical tissue response enhancement of the present invention (including, for instance, stimulation from a power source by conductive, inductive and/or capacitive coupling, electromechanical stimulation, electromagnetic stimulation, and so forth). Portions of the heart valve 292 can create an electric charge or voltage by transducing movement, by blood flow or shear, or by mechanical strain into electricity. Various polarity and/or periodicity can be utilized. For example, in FIG. 29A, a valve 292 is illustrated which displays a charge polarity between opposing surfaces of the valve 292 (designated "1") and a charge polarity between the base and tip of valve 292 (designated "2"). In FIG. 29B, a valve 292 is illustrated in which tissue response is stimulated by providing a charge polarity at the top surface (designated "1") and at the bottom surface (designated "2"), for example, by transducing strain into electricity, as described elsewhere herein. In FIG. 29C, stimulation of tissue response at valve 292 is illustrated in which a charge polarity exists between the valve and a position elsewhere in the body (designated "1"). In FIG. 29D, specific regions of differing potential difference (designated "1" and "2") can be used, for example, to encourage endothelialization in one portion, enhance protein synthesis in another portion, reduce clotting particularly in yet another portion, and so forth. In FIG. 29E, a checkerboard pattern of regions of enhanced tissue response (e.g., due to charge polarity between regions) is shown and could also include stripes, dots, grids, or other patterns. In FIG. 29F, endothelialization of the surface of the valve 292 is enhanced by application of electrical energy applied via source (3), for example, from a power source outside the body via conductive, capacitive and/or inductive coupling strategies. Other variations and combinations in addition to these are clearly possible, depending on the particular effect(s) desired.

Figure 14A:
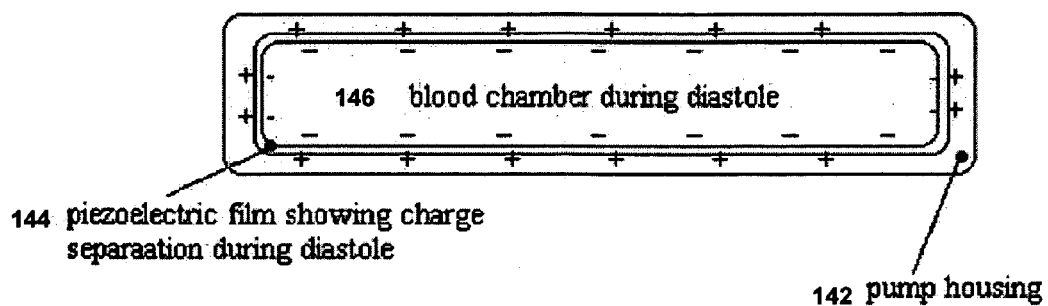
FIGS. 14a and 14b are schematic drawings of a stimulated blood pumping chamber during diastole and systole, respectively, according to an exemplary embodiment of the present invention.
Figure 14B:
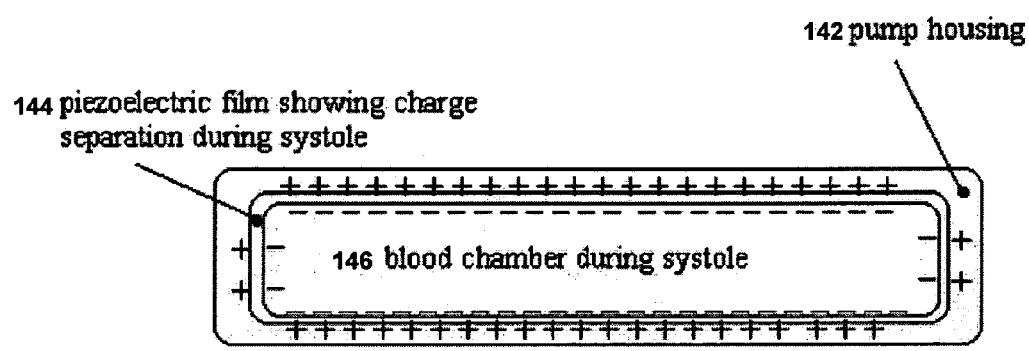

FIGS. 14a and 14b are schematic cross-sectional drawings showing the pumping chamber 146 of a blood pump, which may be, for example, part of a Left Ventricular Assist Device (LVAD) or Totally Artificial Heart (TAH). The film 144 coating the blood contacting chamber 146 and separating it from the pump housing 142 is polarized such that the surface becomes more negative during systole (See FIG. 14b), allowing certain cell types to settle on the surface during the slow flow diastolic portion of the heart cycle (See FIG. 14a). In particular, since in this application there is no contact between the blood pumping surface (i.e., film 144) and native endothelium, it may be desirable to attract cells to the surface from the host blood. In these embodiments, the stimulation charge can be chosen to attract progenitor cells that may differentiate into viable cells (e.g., cells such as fibroblasts, myofibroblasts, SMCs, or ECs) that contribute to the formation of a living surface. (As an alternative, cell growth may be promoted ex vivo prior to implantation.) Optional stimulation mechanisms, for example, using a scheme like that shown in FIG. 23b, may be used to apply a voltage between the surface and the blood.

Figure 30:
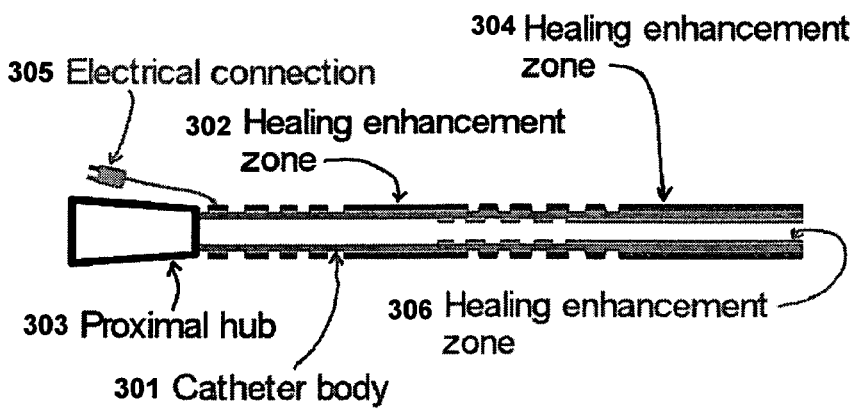
FIGS. 30, 31 and 33a through 33d are schematic drawings that illustrate indwelling electrical stimulation devices, in accordance with various exemplary embodiments of the present invention.

FIG. 30 is a schematic partial cross-sectional illustration of an indwelling catheter of the present invention. The catheter comprises a generally tubular body 301, a proximal hub 303, one or more surface regions having electrical enhancement of tissue response 302, 304, 306. For instance, the regions can be electrically stimulated as described above, e.g., through the use of a conductively, capacitively and/or inductively coupled power source, through electromechanical stimulation, through electromagnetic stimulation, and so forth. In this embodiment, an external electrical connection 305 can readily be provided as indicated. The indwelling catheter is typically introduced into a body vessel or cavity and left to remain in place for several weeks or longer, up to months or years if properly functioning. The indwelling catheter can also be used for the administration of medication, such as administration of chemotherapy, or for blood access for dialysis. The catheter can be placed in a vein, for example, or an artery, or a heart chamber. If desired, two similar catheters can be used, such as one in an artery and one in a vein, or branches of a branched catheter could be located in different vessels, or specific regions can be located in different parts of the same vessel such as for inlet and outlet flow for dialysis. Depending on the particular use, the entire intracorporeal portion may have the enhanced cell stimulation, or only specific portions of the catheter, such as near the distal tip, or near a side opening, can have the enhanced cell stimulation provided by the present invention. Enhanced cell stimulation zones can be provided on the external surface of the device, the internal surface of the device, or a combination. FIG. 30 indicates 3 zones of enhanced cell stimulation or healing enhancement (i.e., two external healing enhancement zones 302, 304 and one internal healing enhancement zone 306), with dashed lines to indicate areas into which the zones may be extended or join one another. Although any of the powering schemes disclosed herein may be utilized, an indwelling catheter is particularly well-suited to an external power source, and can be provided with an electrical connection 305 for attachment to an external power source, as illustrated.

Similar enhanced devices could be used for placement in the kidney, abdomen, thorax, cerebrospinal fluid space, or within other natural or artificial lumens, including those with cell growth modification primarily for cell types other than ECs.

Figure 31:
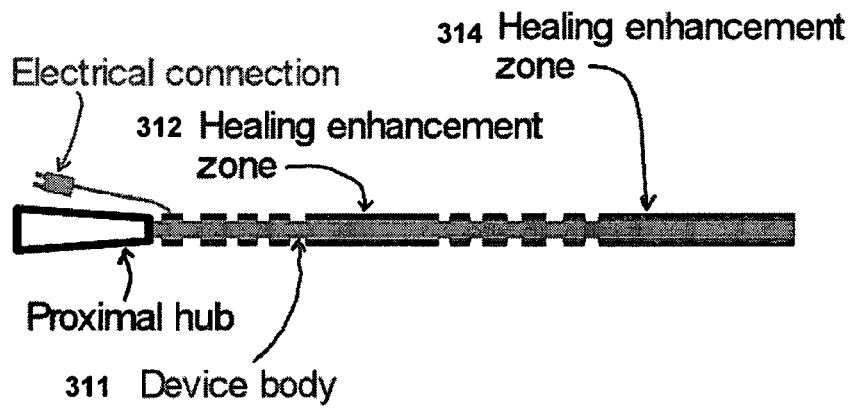

FIG. 31 is a partial cross-sectional schematic illustration of another implantable device in accordance with the present invention. This device has much in common with the device of FIG. 30, and includes a device body 311 and one or more surface regions having electrical enhancement of tissue response 312, 314, but is not necessarily a catheter. For example, a pacemaker lead could have a main body portion, which includes electrical conductor(s), insulator(s), exposed electrode, connector, and may have a cuff or other elements. The implantable device includes one or more regions of electrical enhancement of tissue response. For instance, the regions can be electrically stimulated as described above, e.g., through the use of a conductively, capacitively and/or inductively coupled power source, through electromechanical stimulation, through electromagnetic stimulation, and so forth. For example, a lead which traverses a blood vessel or is placed within a heart chamber is encouraged to endothelialize, discouraged to thrombose, discouraged to fibrose, etc. The region(s) of electrical enhancement of tissue response may need to be electrically isolated from the exposed electrode to avoid interference. Alternatively, a monitoring device such as a device to monitor blood pressure, glucose levels, or other parameters may comprise a main body portion, with the electrical enhancement of tissue response of the present invention provided. Other alternatives include a drug infusion pump, pacemaker or other stimulator generators, and other implantable devices.

Figure 32:
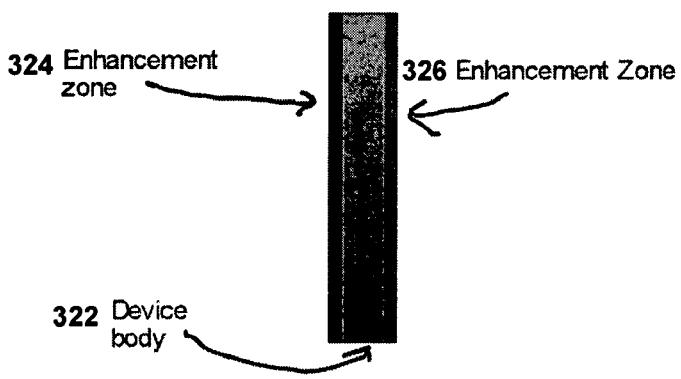
FIG. 32 is a schematic drawing that illustrates an occlusion device, according to an exemplary embodiment of the present invention.

FIG. 32 is a cross-sectional schematic illustration of an implantable occlusion device in accordance with the present invention. The occlusion device is intended to close a vascular opening or mend a tissue. For example, an atrial septal defect, ventricular septal defect, patent foramen ovale, patent ductus arteriosis, atrial appendage, aneurysm, arteriovenous fistula, arteriovenous malformation, and so forth, may require closure or occlusion using an implanted device. Such an implanted device includes a main body 322 which performs a structural role in closing the feature, and may have struts, supports, hooks, fasteners, or other mechanisms as are known in the art. The present inventive device incorporates one or more regions of enhanced tissue response 324, 326. The desired tissue response may include a rapid thrombotic occlusion, rapid tissue ingrowth, and/or rapid endothelialization. The main body 322 may be porous, and electrical enhancement of tissue ingrowth into the pores may be effected by the present invention, alone, or in combination with one or more surface regions which have enhanced tissue response. For example, the surface region(s) may have similar desired tissue response, but preferably the surface regions provide for endothelialization to prevent thrombus formation on the surface, while the main body, if porous, may require thrombotic or cellular or proteinaceous occlusion to affect the occlusive seal provided by the device after implant.

Figure 33A:
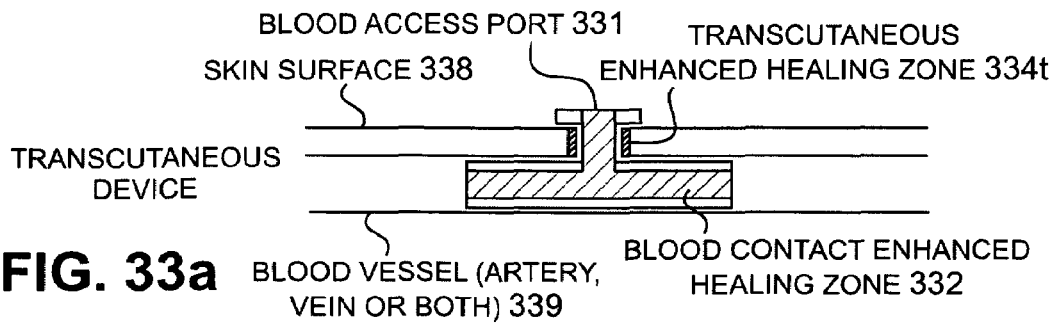
Figure 33B:
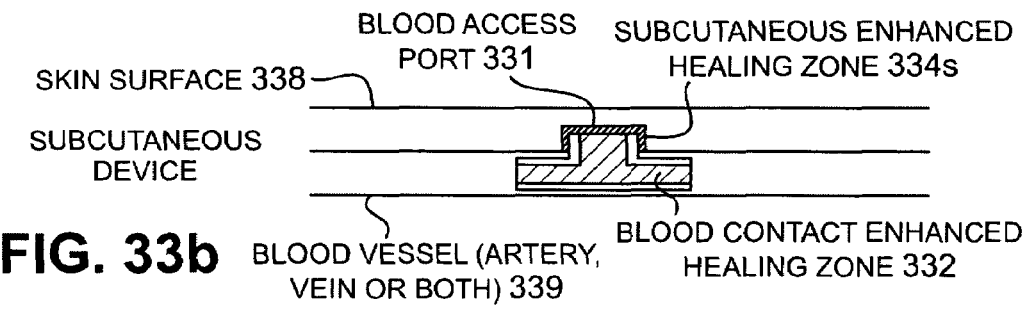
Figure 33C:
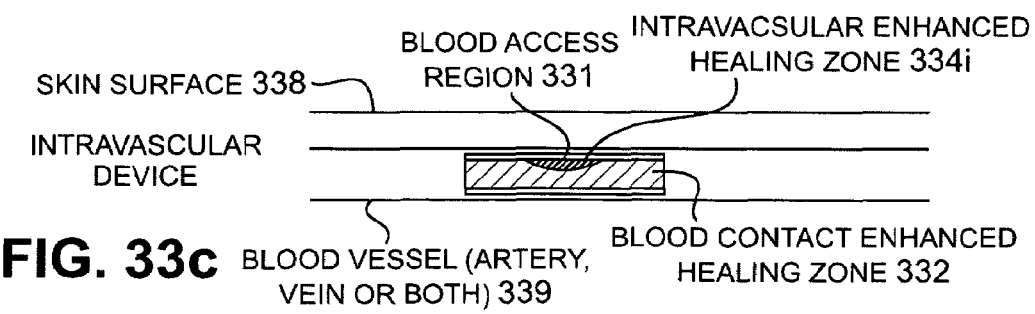
Figure 33D:
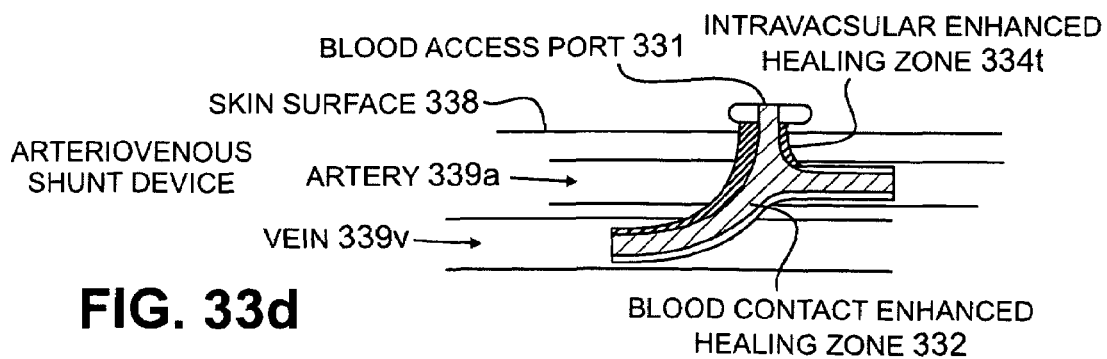

FIGS. 33a through 33d are schematic cross-sectional illustrations of transcutaneous implantable devices in accordance with the present invention. The devices are designed to occupy, for example, a blood vessel 339, such as a vein 339v, and artery 339a, or both, beneath the skin surface 338. Each device includes a blood access port 331, and a blood contact enhanced healing zone 332. These devices also include a transcutaneous enhanced healing zone 334t (FIGS. 33a and 33d), a subcutaneous enhanced healing zone 334s (FIG. 33b), or an intravascular enhanced healing zone 334i (FIG. 33c). Hence, the devices can, for example, be configured with a transcutaneous blood access port for hemodialysis, medication infusion, blood or other fluid sampling, and so forth. The deeper portion can be implanted into a blood vessel, or can be implanted as a shunt between an artery and a vein. The superficial portion can be implanted so that it is transcutaneous. One or more portions of the devices have stimulation of tissue response according to the present invention. For example, electrical stimulation of skin healing at a transcutaneous zone may be utilized; and/or electrical stimulation of endothelialization or inhibition of hyperplasia at intravascular zone(s) may be utilized. Alternatively, the superficial portion of the device can be implanted so that it is subcutaneous; in this case, electrical stimulation of fibroblasts or other cells involved in healing can be incorporated to heal the tissue adjacent to an access zone, for example. The various zones or regions can have differing stimulation polarity, amplitude, pulsatility, and so forth if desired to achieve differing tissue response in the various zones or regions. Still another alternative is to implant the device entirely with a vessel, with a zone of enhanced healing for blood access.

Figure 34A:
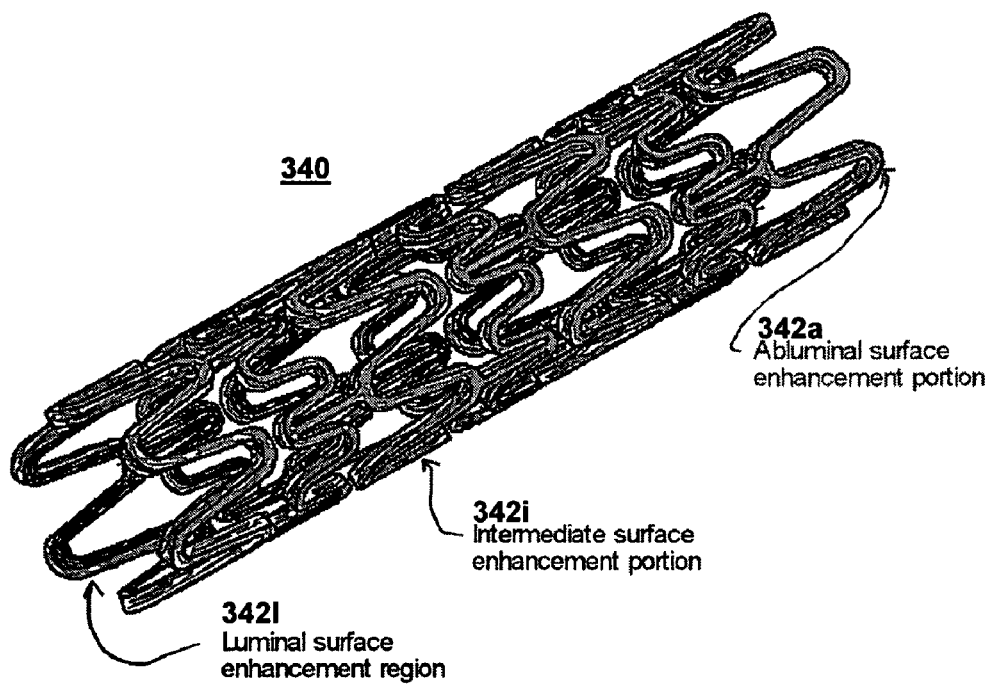
FIGS. 34a and 34b are schematic drawings that illustrate intravascular stents for surface charge stimulation, according to two exemplary embodiments of the present invention.
Figure 34B:
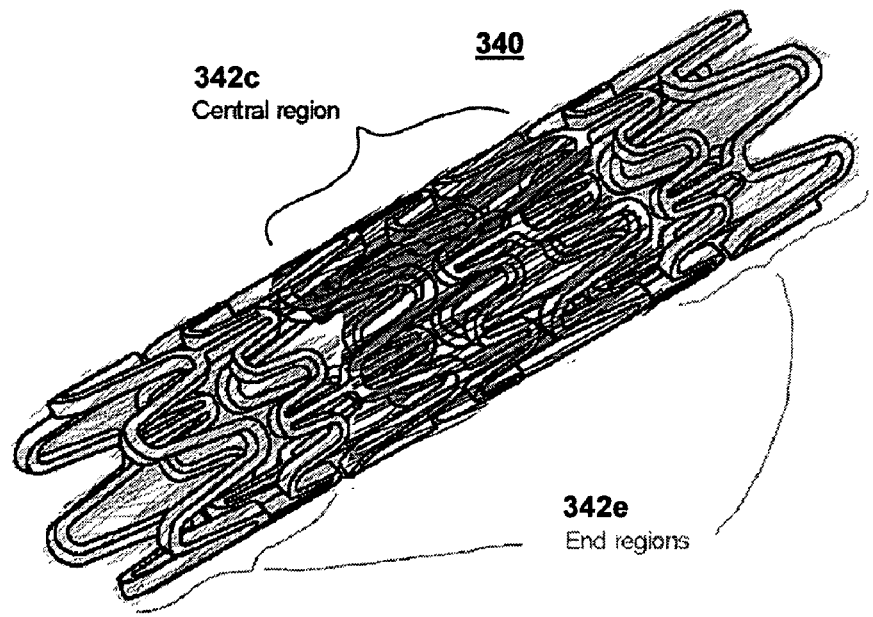

FIGS. 34a and 34b are schematic illustrations of intravascular stent devices 340 in accordance of the present invention. The intravascular stent devices 340 are intended to prop open a body lumen, such as a blood vessel. Enhanced tissue response can be provided by the present invention, for example, to encourage rapid endothelialization of the blood-contact surfaces, or to reduce tissue hyperplasia or restenosis, or both. Electrical stimulation can be applied to the entirety of the stent, or to only a portion there of. For example, electrical stimulation can be applied at differing radial portions of the stent device such as the luminal surface 342l and/or the abluminal surface 342a and/or the lateral surfaces 342i intermediate the luminal 342l and abluminal 342a surfaces. Moreover, different portions of the stent device 340 can have different electrical stimulation to effect enhancement of different types of cellular response. For example, the voltage, polarity, and waveform can be optimized to encourage rapid endothelialization on the luminal 342l and intermediate 342i surfaces, while voltage, polarity, and waveform can be optimized on the abluminal surface 342a to reduce SMC proliferation or inflammation associated with restenosis. The voltage, polarity, and waveform requirements can be different for the different regions. Alternatively, only a portion of the device can have the electrical stimulation for tissue response enhancement. Yet another alternative is to define portions along the axial length of the device, such as end regions 342e and a central region 342c, which may have different electrical stimulation to achieve different types of cellular response.

Figure 35:
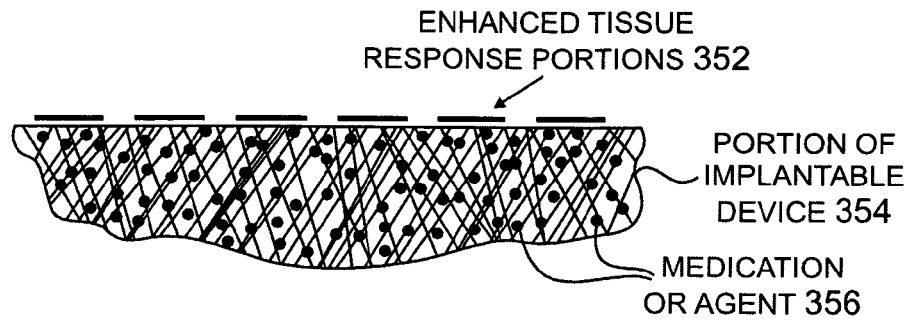
FIG. 35 is a schematic drawing showing a portion of a device which combines surface charge stimulation and drug delivery, according to an exemplary embodiment of the present invention.

FIG. 35 schematically illustrates a device 354 having electrical stimulation for enhanced tissue response and also having drug or agent delivery. A portion of the device 354 is illustrated; the device can be a vascular graft, catheter, occlusion device, healing device, skin patch, myocardial patch, or other device, including those described elsewhere herein. The surface is shown to have one or more portions 352 which provide electrical stimulation for enhanced tissue response in accordance with the present invention (including stimulation from a power source by conductive, capacitive and/or inductive coupling, electromechanical stimulation, electromagnetic stimulation, and so forth); in other embodiments, disposing the portions providing electrical stimulation within the body of the device may also be advantageous as discussed above. In combination with the tissue response enhancement by electrical stimulation of the present invention, medications or agents 356 may be incorporated with the device 354 to further enhance the performance of the device. For example, a variety of drugs used to modulate tissue response can be incorporated into a polymer, as a coating, in time-release or delayed-release configurations, as filler, or using other mechanisms and methods of drug-loading of devices as are known in the art. For example, an agent which reduces hyperplasia or limits collagen deposition may be used, together with electrical endothelial stimulation, to provide a synergistic enhancement of tissue response, such as for an intravascular implant, such as a graft or patch. Another example is a pacemaker lead where electrical tissue response enhancement may be used together with steroid elution to limit fibrosis which would otherwise decrease effectiveness of the pacemaker lead. Numerous other advantageous configurations are clearly possible, including further enhancement of the various devices described herein, by adding medication or other agent which can reside in or on a device, for example, for presentation to tissue or for elution from the device.

"Therapeutic agents", "pharmaceutically active agents", "pharmaceutically active materials", "drugs" and other related terms may be used interchangeably herein and include genetic and non-genetic therapeutic agents.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking SMC proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; and (r) hormones; and (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin.

Specific non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel and Ridogrel, among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, (e) thymidine kinase ("TK") and other agents useful for interfering with cell proliferation, and (f) DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., PCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Figure 36:
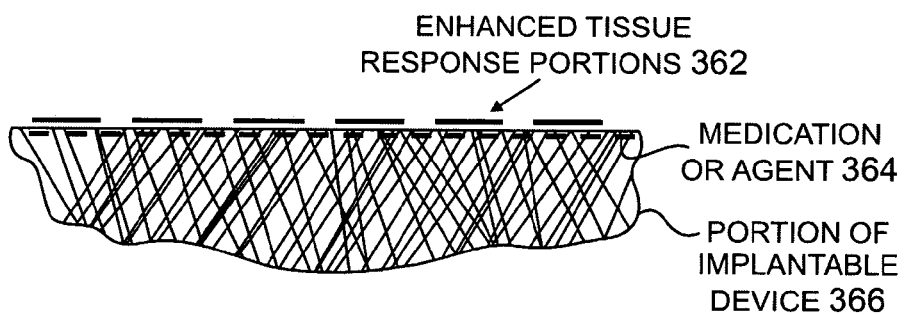
FIG. 36 is a schematic drawing showing a portion of a device which combines surface charge stimulation and drug delivery facilitation, according to an exemplary embodiment of the present invention.

FIG. 36 schematically illustrates a device having electrical stimulation for enhanced tissue response and also utilizing electrical (e.g., electrostatic) modulation of drug or agent retention or release. A portion of the device 364 is illustrated; the device can be a vascular graft, catheter, occlusion device, healing device, skin patch, myocardial patch, or other device, including those described elsewhere herein. The surface is shown to have one or more portions 362 incorporating enhanced tissue response of the present invention; in other applications enhancement of tissue response within the body of the device may also be advantageous as previously discussed. In combination with the tissue response enhancement by electrical stimulation of the present invention (including, for example, stimulation from a power source by inductive and/or capacitive coupling, electromechanical stimulation, electromagnetic stimulation, and so forth), medications or agents 364 may be incorporated with the device to further enhance the performance of the device, where electrical or electromagnetic stimulation provides modulation of the activity or release of the medications or agents. For example, a drug may be attached to or detached from a surface by use of electrostatic forces provided in accordance with the present invention.

In another example, a chemical reaction which causes activation, inactivation, retention, or release of one or more agents or components may be stimulated or inhibited by electrical or electromagnetic forces or stimulations provided in accordance with the present invention.

In another example, biological responses such as calcification, lipid accumulation, thrombosis or thrombolysis, enzyme activation modulation, complement or immune system activation or inactivation, or other biological or tissue response modulation can be accomplished by utilizing electrical or electromagnetic stimulation provided in accordance with the present invention. For example, an implantable device having electrical stimulation can be implanted in the vicinity of a vascular plaque to reduce lipid accumulation, or in the vicinity of a joint to reduce extracellular calcification, or in the vicinity of healing tissue to modulate the white cell activity to enhance healing.

Various aspects and components in the various illustrated embodiments may be combined, and the teachings may be applied to treatment of other body tissues even if not explicitly cited herein, while still being within the scope of the present invention and disclosure.

Many of the embodiments described above envision electrical stimulation of a prior art device, such as a synthetic valve or stent, to enhance endothelialization and healing. However, devices designed primarily for the purpose of healing a damaged, blood-contacting, native surface are also part of this invention.

Figure 37:
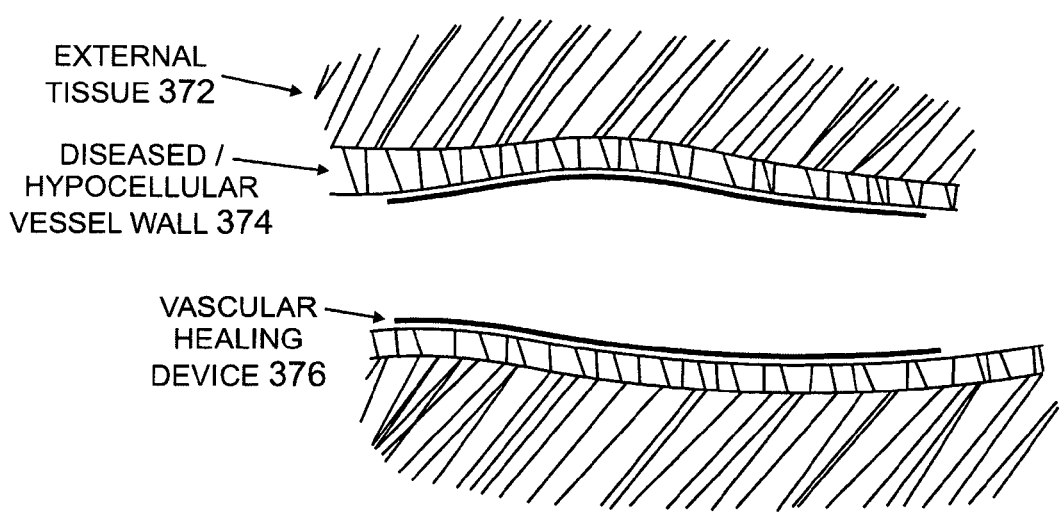
FIG. 37 is a schematic drawing showing stimulation of native tissues for healing, using a vascular device in accordance with an exemplary embodiment of the present invention.

For example, FIG. 37 schematically illustrates a vascular healing device having electrical tissue response enhancement of the present invention. The device can be used, for example, to enhance the healing of an aorta to prevent or reduce aneurysmal expansion. The vascular healing device incorporates electrical enhancement of tissue response of the present invention. FIG. 37 illustrates a portion of a body vessel such as an aorta which is starting to become aneurysmal due to disease and/or hypocellularity. The vascular healing device 376 of the present invention utilizes electrical stimulation (including stimulation from a power source by conductive, capacitive and/or inductive coupling, electromechanical stimulation, electromagnetic stimulation, and so forth) to enhance tissue response such as by enhancing cellular proliferation, migration, secretion, synthesis, or stabilization. For example, cells can be encouraged to migrate from the surrounding healthier tissue 372 external to the diseased portion of the body vessel 374. Cells or precursor cells can also be encouraged to deposit from the blood. The enhanced tissue response can provide for strengthening of the body vessel to reduce or stop progression of aneurysmal dilatation, or even to provide regression of an aneurysmal dilatation.

Appropriate polarity and distribution of stimulation as provided by the various embodiments and aspects of the present invention are incorporated into the vascular healing device to encourage granulation tissue, fibroblast ingrowth and collagen synthesis, SMC proliferation and protein synthesis, modulation of inflammatory response, proliferation of ECs, and other tissue enhancements including those elsewhere described in the present disclosure. The vascular healing device, for example, can take the form of a stent or stent-graft, can provide structural support, or can simply be applied to the body vessel while the body vessel itself provides any required structural support. The vascular healing device is preferably porous or discontinuous to facilitate tissue growth to the lumen and provide for patency of branch vessels; a variety of porous and non-porous structures are possible as described herein.

As in the other embodiments described herein, an electrical stimulation of appropriate polarity, amplitude and time dependency can be provided between regions of the vascular healing device, between the vascular healing device and the body vessel, between the vascular healing device and the external tissue, and so forth. Electrical stimulation of charge or field may be applied from local components at or near the implanted vascular healing device, or may be applied from an implanted or non-implanted source distant to the vascular healing device and coupled by electrical conductor(s) or by inductive or capacitive coupling. Electrical stimulation may also be applied using electromechanical materials, such as piezoelectric or electroactive components.

While electromechanical transducing materials such as piezoelectric films are envisioned as stimulation entities in many of the above applications, there are many implant sites within the body for which a mechanical energy source of sufficient strength to adequately polarize the film is not available. For example, implants on the low pressure venous return system may not have sufficient blood pressure variation to drive piezoelectric films. Examples of implant devices in the venous system include blood filters and venous valves. Hence, devices in such locations may require a separate stimulation power source and control system, such as those described in FIGS. 10 and 11, among others.

SUMMARY

Although various embodiments are specifically illustrated and described herein, it will be appreciated that modifications and variations of the invention are covered by the above teachings and are within the purview of the appended claims without departing from the spirit and intended scope of the invention. For example, various power sources for introduction of surface charge are shown, however, others may be employed without departing from the scope of the invention. Moreover, geometric configurations are typically shown to be tubular and planar, however, many other configurations, including more complex configurations, are also possible without departing from the scope of the invention. Furthermore, these examples should not be interpreted to limit the modifications and variations of the invention covered by the claims but are merely illustrative of some possible variations.

Moreover, while various theories of operation are set forth herein, the invention is not bound by such theories. Furthermore, while various theoretical calculations have been made herein, it should be understood that values in actual practice may deviate significantly from calculated values. Such calculations are nonetheless useful for purposes of predicting feasibility, and they provide those of ordinary skill in the art with information for developing prototypical devices, which should greatly reduce the effort required to develop effective products for various applications.

What is claimed is:

1. A medical device comprising a first medical device portion comprising a first tissue contacting surface that is configured to undergo a time-dependent variation in surface charge at a site of contact with a host, in response to a time-dependent signal, wherein said first tissue contacting surface undergoes said time-dependent variation in surface charge using energy provided by said host, and said first tissue contacting surface is configured to experience a phasic variation in strain when in contact with said host and wherein said first tissue contacting surface comprises a material that produces a surface charge in response to mechanical deformation due to said phasic variation in strain.

2. The medical device of claim 1, wherein said variation in surface charge mimics surface charge variations that lead to enhanced or inhibited cellular growth in the natural environment with which the device is configured to make contact.

3. The medical device of claim 2, wherein said time-dependent signal comprises an electrocardial signal or a blood flow signal.

4. The medical device of claim 1, wherein said time-dependent variation in surface charge is produced based on a time-dependent signal that is provided by the host.

5. The medical device of claim 2, wherein said time-dependent signal comprises a signal that varies periodically with a heartbeat.

6. The medical device of claim 5, wherein said first tissue contacting surface is a blood contacting region that has a negative surface charge during a first portion of said signal and a less negative or non-negative surface charge during a second portion of said signal.

7. The medical device of claim 6, wherein the first portion of the signal is synchronized with a period of increased blood pressure and the second portion of the signal is synchronized with a period of decreased blood pressure.

8. The medical device of claim 6, wherein said first tissue contacting surface has a non-negative surface charge during said second portion of said signal.

9. The medical device of claim 8, wherein said non-negative surface charge is a neutral surface charge.

10. The medical device of claim 8, wherein non-negative surface charge is a positive surface charge.

11. The medical device of claim 2, wherein said time-dependent signal comprises a blood pressure signal.

12. The medical device of claim 1, further comprising an electrical stimulator that generates said variation in surface charge, said stimulator comprising a power source.

13. The medical device of claim 12, wherein said stimulator is implanted in said host.

14. The medical device of claim 13, wherein said stimulator is capacitively or inductively rechargeable.

15. The medical device of claim 12, wherein said stimulator is external to said host.

16. The medical device of claim 15, wherein said stimulator is conductively, capacitively or inductively coupled to said medical device.

17. The medical device of claim 12, wherein said stimulator further comprises a processor.

18. The medical device of claim 17, wherein said processor generates said time-dependent variation in surface charge.

19. The medical device of claim 12, further comprising a sensor that senses said signal from said host, wherein said stimulator provides said variation in suffice charge in synchronization with said signal from said host.

20. The medical device of claim 19, wherein said sensor is implanted within said host.

21. The medical device of claim 19, wherein said sensor is external to said host.

22. The medical device of claim 12, wherein said first medical device portion comprises a first electrode disposed at or beneath said first tissue contacting surface, which provides said time-dependent variation in surface charge, said time-dependent variation in surface charge being effective to enhance or inhibit cellular growth adjacent to, on, or within said first tissue contacting surface.

23. The medical device of claim 22, wherein said first medical device portion further comprises a second tissue contacting surface which is configured to undergo a time-dependent variation in surface charge at a site of contact with said host, said second time-dependent variation in surface charge being effective to enhance or inhibit cellular growth adjacent to, on, or within said second tissue contacting surface, and a second electrode disposed at or beneath said second tissue contacting surface, which provides said time-dependent variation in surface charge at said second tissue contacting surface.

24. The medical device of claim 23, wherein said first and second electrodes each comprise one or more conductive filaments.

25. The medical device of claim 23, wherein said first and second electrodes each comprise a patterned conductive film.

26. The medical device of claim 22, wherein said first medical device portion further comprises a second electrode that is disposed within said first medical device portion and is substantially electrically isolated from said host.

27. The medical device of claim 26, wherein said device further comprises: a polymer film having a first surface which contacts said host and a second surface opposite said first surface which does not contact said host, and wherein said first electrode is buried within said film proximate said first surface; and said second electrode is buried within said film proximate said second surface.

28. The medical device of claim 22, wherein said medical device comprises a second medical device portion, which comprises a second tissue contacting surface which is configured to undergo a time-dependent variation in surface charge at a site of contact with said host, and a second electrode disposed at or beneath said second tissue contacting surface, which provides said time-dependent variation in surface charge at said second tissue contacting surface.

29. The medical device of claim 28, wherein said first medical device portion is a vascular implant and said second medical device portion is adapted to make contact with solid tissue proximate said implant or with blood proximate said implant.

30. The medical device of claim 22, wherein said first electrode is arranged in a manner that mimics an arrangement of native cells in the natural environment with which the device is configured to make contact.

31. The medical device of claim 22, wherein said first electrode comprises one or more conductive filaments.

32. The medical device of claim 22, wherein said first electrode comprises a patterned conductive film.

33. The medical device of claim 1, where said material is a piezoelectric or electrostrictive material.

34. The medical device of claim 33, wherein said device comprises a piezoelectric or electrostrictive film having a blood contacting surface.

35. The medical device of claim 34, wherein the polarity of said film is such that said blood contacting surface becomes negatively charged in response to increasing pressure.

36. The medical device of claim 34, wherein said piezoelectric or electrostrictive film generates a surface charge variation with a variation in blood pressure that mimics surface charge variations that occur on native cell membranes.

37. The medical device of claim 34, wherein said piezoelectric or electrostrictive film includes an internal resistance that provides a high-pass filter time constant of between approximately two seconds and approximately one hundred seconds.

38. The medical device of claim 34, wherein said film is a piezoelectric polymer film.

39. The medical device of claim 34, wherein said film is a piezoelectric polyvinylidene fluoride (PVDF) copolymer film.

40. The medical device of claim 39, wherein said film has a thickness between approximately 0.1 microns and approximately 10 microns.

41. The medical device of claim 34, wherein said film is provided in a predetermined pattern.

42. The medical device of claim 41, wherein said predetermined pattern mimics an arrangement of native cells in the natural environment with which the device is configured to make contact.

43. The medical device of claim 41, wherein the medical device comprises a lumen through which blood flows, and wherein the predetermined pattern comprises elongated segments that are oriented circumferentially with respect to said lumen, or both axially and circumferentially with respect to said lumen.

44. The medical device of claim 41, wherein the medical device comprises a lumen through which blood flows, and wherein the pattern mimics the arrangement of smooth muscle cells in native blood carrying lumens.

45. The medical device of claim 41, wherein said predetermined pattern comprises multiple elongated segments having lengths of 100 to 1000 microns and widths of 2 to 20 microns.

46. A method for manufacturing the medical device of claim 34, comprising: providing a medical device; and applying a piezoelectric or electrostrictive polymer film on a blood-contacting surface of the medical device.

47. The method of claim 46, further comprising etching the film in a predetermined pattern.

48. The medical device of claim 1, wherein said phasic variation in strain is due to a phasic variation in blood pressure.

49. The medical device of claim 1, wherein said first tissue contacting surface is provided with a d.c. bias potential.

50. The medical device of claim 49, wherein said d.c. bias potential is provided by including molecular species at said first tissue contacting surface that exhibit a charge when said first tissue contacting surface is contacted with said host.

51. The medical device of claim 49, wherein said first medical device portion comprises a first electrode disposed at or beneath said first tissue contacting surface which provides said time-dependent variation in surface charge, and wherein said d.c. bias potential is provided by imposing a d.c. bias voltage on said first electrode.

52. The medical device of claim 1, wherein said device is selected from a vascular graft, a blood pump comprising a blood contacting chamber, an implantable drug infusion pump, a heart valve, a venous valve, a vascular stem, a blood filter, a pacemaker, a pacemaker lead, a wound bandage, an indwelling catheter, a vascular healing device, an occlusion device, a myocardial patch, and a blood access device.

53. The medical device of claim 1, wherein said first medical device portion of said medical device is adapted for implantation in a body lumen.

54. The medical device of claim 53, wherein said medical device comprises luminal and abluminal surfaces that undergo time-dependent variations in surface charge that differ from one another in polarity, amplitude, phase, or a combination thereof.

55. The medical device of claim 1, wherein said variation in surface charge is provided by generating an electrical potential between said first tissue contacting surface and an interior region of said first medical device portion that is substantially electrically isolated from said host.

56. The medical device of claim 1, wherein said variation in surface charge is provided by generating an electrical potential between said first tissue contacting surface and a second tissue contacting surface of said first medical device portion.

57. The medical device of claim 56, wherein said first and second tissue contacting surfaces are on opposite sides of said device.

58. The medical device of claim 1, wherein said variation in surface charge is provided by generating an electrical potential between said first tissue contacting surface and a location within the body of the host.

59. The medical device of claim 1, wherein said device further comprises a therapeutic agent that is released in said host.

60. The medical device of claim 59, wherein said therapeutic agent assists said surface charge in enhancing or inhibiting cellular growth.

61. The medical device of claim 59, wherein said device is adapted to electrically modulate release of said therapeutic agent.

62. The medical device of claim 1, wherein said tissue contacting region is a porous region.

63. A medical device comprising a first medical device portion comprising a first tissue contacting surface that is configured to undergo a time-dependent variation in surface charge at a site of contact with a host, in response to a time dependent signal, wherein said first tissue contacting surface undergoes said time-dependent variation in surface charge using energy provided by said host; and wherein said first tissue contacting surface is exposed to an ion containing bodily fluid that undergoes a phasic variation in flow velocity and wherein said implant provides a magnetic field that is perpendicular to the direction of said flow.

64. A method of treatment comprising implanting the medical device of claim 1 into a host.

65. A medical device comprising a first medical device portion comprising a first tissue contacting surface that is configured to undergo a time-dependent variation in surface charge at a site of contact with a host, in response to a time-dependent signal, wherein said non-negative surface charge is a neutral surface charge.

66. A medical device comprising a first medical device portion comprising a first tissue contacting surface that is configured to undergo a time-dependent variation in surface charge at a site of contact with a host, in response to a time-dependent signal, an electrical stimulator that generates said variation in surface charge, said stimulator comprising a power source, wherein said first medical device portion comprises a first electrode disposed at or beneath said first tissue contacting surface, which provides said time-dependent variation in surface charge, said time-dependent variation in surface charge being effective to enhance or inhibit cellular growth adjacent to, on, or within said first tissue contacting surface, and wherein said first electrode comprises one or more conductive filaments.

67. A medical device further comprising an electrical stimulator that generates said variation in surface charge, said stimulator comprising a power source, wherein said first medical device portion comprises a first electrode disposed at or beneath said first tissue contacting surface, which provides said time-dependent variation in surface charge, said time-dependent variation in surface charge being effective to enhance or inhibit cellular growth adjacent to, on, or within said first tissue contacting surface, and wherein said first medical device portion further comprises a second tissue contacting surface which is configured to undergo a time-dependent variation in surface charge at a site of contact with said host, said second time-dependent variation in surface charge being effective to enhance or inhibit cellular growth adjacent to, on, or within said second tissue contacting surface, and a second electrode disposed at or beneath said second tissue contacting surface, which provides said time-dependent variation in surface charge at said second tissue contacting surface, wherein said first and second electrodes each comprise one or more conductive filaments.

68. A medical device comprising a first medical device portion comprising a first tissue contacting surface that is configured to undergo a time-dependent variation in surface charge at a site of contact with a host, in response to a time-dependent signal, wherein said first tissue contacting surface is provided with a d.c. bias potential and wherein said first medical device portion comprises a first electrode disposed at or beneath said first tissue contacting surface which provides said time-dependent variation in surface charge, and wherein said d.c. bias potential is provided by imposing a d.c. bias voltage on said first electrode.

69. A method for manufacturing a medical device comprising a piezoelectric or electrostrictive film having a blood contacting surface and further comprises a first medical device portion comprising a first tissue contacting surface that is configured to undergo a time-dependent variation in surface charge at a site of contact with a host, in response to a time-dependent signal comprising:
providing a medical device;
applying a piezoelectric or electrostrictive polymer film on a blood-contacting surface of the medical device, and
further comprising etching the film in a predetermined pattern.

* * * * *